(12) United States Patent
Alexander et al.

(10) Patent No.: US 10,791,978 B2
(45) Date of Patent: Oct. 6, 2020

(54) CLASSIFYING INDIVIDUALS USING FINITE MIXTURE MARKOV MODELLING AND TEST TRIALS WITH ACCOUNTING FOR ITEM POSITION

(71) Applicant: Medical Care Corporation, Newport Beach, CA (US)

(72) Inventors: Gregory E. Alexander, Irvine, CA (US); William Rodman Shankle, Corona del Mar, CA (US)

(73) Assignee: Medical Care Corporation, Newport Beach, CA (US)

( * ) Notice: Subject to any disclaimer, the term of this patent is extended or adjusted under 35 U.S.C. 154(b) by 0 days.

(21) Appl. No.: 16/459,099

(22) Filed: Jul. 1, 2019

(65) Prior Publication Data

US 2020/0069229 A1     Mar. 5, 2020

Related U.S. Application Data

(63) Continuation of application No. 15/115,901, filed as application No. PCT/US2015/015282 on Feb. 10, 2015, now Pat. No. 10,335,079.

(Continued)

(51) Int. Cl.
*A61B 5/16* (2006.01)
*G06N 20/00* (2019.01)
(Continued)

(52) U.S. Cl.
CPC .............. *A61B 5/16* (2013.01); *A61B 5/165* (2013.01); *A61B 5/4088* (2013.01);
(Continued)

(58) Field of Classification Search
CPC ....... A61B 5/16; A61B 5/4088; A61B 5/7264; G16H 50/20; G16H 10/20; G16H 50/50; G06N 99/005
See application file for complete search history.

(56) References Cited

U.S. PATENT DOCUMENTS 6,832,069 B2   12/2004   Stout
8,202,095 B2    6/2012   Shankle
(Continued)

OTHER PUBLICATIONS

Broder, et al. "Different storage and retrieval deficits in normal aging and mild cognitive impairment: A multinomial modeling analysis", Psychology and aging, Jun. 2008, 43 pages.
(Continued)

*Primary Examiner* — Vanthu T Nguyen
(74) *Attorney, Agent, or Firm* — Fish & Richardson P.C.

(57) ABSTRACT

Methods, systems, and apparatus, including medium-encoded computer program products, for analyzing data include: receiving data including responses, and lack thereof, for items of a cognitive test including multiple item-recall trials; processing the data using a stochastic model of a cognitive process, in which a conditional probability distribution of future states of the cognitive process depend upon a present state; and encoding a result of the processing on a non-transitory computer-readable medium for use in an assessment related to cognition; wherein the processing using the stochastic model includes representing recall or recognition of an item in the multiple item-recall trials using distinct cognitive states; and wherein the processing using the stochastic model includes adjusting separate memory storage and retrieval parameters for each of the distinct cognitive states in the modeled cognitive process to account for position of the items in each respective trial of the multiple item-recall trials.

27 Claims, 26 Drawing Sheets

Related U.S. Application Data

(60) Provisional application No. 61/938,045, filed on Feb. 10, 2014.

(51) Int. Cl.
*G16H 10/20* (2018.01)
*G16H 50/50* (2018.01)
*G16H 50/20* (2018.01)
*A61B 5/00* (2006.01)

(52) U.S. Cl.
CPC .......... *A61B 5/7264* (2013.01); *G06N 20/00* (2019.01); *G16H 10/20* (2018.01); *G16H 50/20* (2018.01); *G16H 50/50* (2018.01)

(56) References Cited

U.S. PATENT DOCUMENTS

| | | |
|---|---|---|
| 9,367,666 B2 | 6/2016 | Shankle et al. |
| 2005/0196735 A1 | 8/2005 | Buschke |
| 2008/0070207 A1 | 3/2008 | Avidan |
| 2009/0298025 A1 | 12/2009 | Raber |
| 2009/0313047 A1 | 12/2009 | Smith |
| 2010/0092929 A1 | 4/2010 | Hallowell et al. |
| 2011/0060715 A1 | 3/2011 | Shankle |
| 2013/0338526 A1 | 12/2013 | Howard |
| 2014/0163426 A1 | 6/2014 | Alberts |

OTHER PUBLICATIONS

International Search Report/Written Opinion issued by USPTO as ISA in PCT/US2015/015282, dated May 29, 2015, 8 pages.

| Trial 1 Study-Test | Trial 2 Study-Test | Trial 3 Study-Test | Trial 4 Delayed Test |
|---|---|---|---|
| U | U | U | U |
| U | U | I | I |
| U | U | L | L |
| U | I | I | I |
| U | I | L | L |
| U | L | L | L |
| I | I | I | I |
| I | I | L | L |
| I | L | L | L |
| L | L | L | L |

FIG. 5D

| Study-Test Trial 1 | Study-Test Trial 2 | Study-Test Trial 3 | Study-Test Trial 4 | Study-Test Trial 5 | Delayed Test Trial 6 | Delayed Test Trial 7 |
|---|---|---|---|---|---|---|
| U | U | U | U | U | U | U |
| U | U | U | U | I | U | U |
| U | U | U | U | L | L | L |
| U | U | U | I | I | U | U |
| U | U | U | I | L | L | L |
| U | U | U | L | L | L | L |
| U | U | I | I | I | | |
| U | U | I | I | L | L | L |
| U | U | I | L | L | L | L |
| U | U | L | L | L | L | L |
| U | I | I | I | I | | |
| U | I | I | I | L | L | L |
| U | I | I | L | L | L | L |
| U | I | L | L | L | L | L |
| U | L | L | L | L | L | L |
| I | I | I | I | I | | |
| I | I | I | I | L | L | L |
| I | I | I | L | L | L | L |
| I | I | L | L | L | L | L |
| I | L | L | L | L | L | L |
| L | L | L | L | L | L | L |

FIG. 5E

CLASSIFYING INDIVIDUALS USING FINITE MIXTURE MARKOV MODELLING AND TEST TRIALS WITH ACCOUNTING FOR ITEM POSITION

This application is a continuation of U.S. patent application Ser. No. 15/115,901, filed Aug. 1, 2016 and issued on Jul. 7, 2019 as U.S. Pat. No. 10,335,079, which is a U.S. National Stage of International Application No. PCT/US2015/015282, filed Feb. 10, 2015, which claims benefit under 35 U.S.C. § 119(e)(1) of U.S. Provisional Application No. 61/938,045, filed Feb. 10, 2014, the entire contents of which is incorporated by reference herein.

BACKGROUND

This specification relates to assessing the cognition of a person, such as can be done based on results of a cognitive test that has been administered to the person.

Among the behavioral manifestations of Alzheimer's disease (AD) and other cognitive disorders are a decline in ability to perform tasks dependent upon learning, retention and retrieval or use of newly learned information acquired within the past two weeks. Item recall tasks have been widely used to assess this cognitive ability. Cognitive processes involved in item recall tasks include attention, encoding, storage into working memory in the prefrontal cortex, plus transfer, encoding and storage of items into short-term memory in the hippocampus and other medial temporal lobe structures. Items can be retrieved from working memory for periods of less than one minute, whereas they can be retrieved from short-term memory for periods between two minutes and two weeks. The items themselves can consist of words, sounds, numbers, characters, syllables, images, locations, or odors.

Item recall tasks are composed of a number of study trials and/or study-test trials, plus test trials, in which a subject learns and recalls a list of n items. A study trial is one in which a subject is presented a list of items in some specified order, and attempts to learn them. A test trial is one in which a subject is asked to correctly recall or identify the items. There are several types of these trials. A study-test trial is a study trial followed by a test trial. A delayed free recall test trial is one in which there is no study trial and the subject is asked, after some delay, to freely recall the list of items from previous study trials without being provided any cues, hints or reminders. A cued recall test trial is one in which the subject is given a cue, hint or reminder for each item from the study trials, and is asked to recall the item based on that information. A recognition test trial is one in which the subject is presented the list of items from the study trial intermixed with a list of items that were not presented in the study trials, and is asked to identify which items came from the study trials and which items did not.

Of those tasks, free recall tasks have become an important part of clinical testing for the detection of AD, which impairs free recall tasks in the earliest clinical stage of the disease process, also known as mild cognitive impairment (MCI). Clinicians and researchers have used free recall tasks for AD diagnostic purposes to detect early, monitor progression, assess severity of impairment, and measure treatment effect, with mixed results. In some cases, using aggregate performance scores, some researchers have failed to discover differences between study groups, such as finding no difference in AD or vascular dementia (VD) patients using the immediate free recall trials from the Consortium to Establish a Registry for Alzheimer's Disease (CERAD) test battery. In contrast, some other researchers have demonstrated that application of a Markov Model was able to identify different memory processes indicative of AD or VD from the CERAD immediate recall task data.

SUMMARY

This specification describes technologies relating to assessing the cognition of a person, such as can be done based on results of a cognitive test that has been administered to the person. Rather than use ad-hoc aggregate performance scores, more detailed statistics can be used to measure subject memory performance on free recall tasks, which take into account additional structure details in the recall task data. These statistics can be designed to measure the underlying cognitive processes involved in recall task performance, which can improve sensitivity of the cognitive assessment process and help in discovering differences between study groups.

The development of better AD therapeutics is moving the field towards earlier detection of its MCI, and even of its pre-MCI stages. The systems and techniques described herein can improve the methods used to analyze memory performance tasks, which can foster earlier detection of MCI. These methods can include the development and application of Hidden Markov Models (HMMs) to identify and measure cognitive processes involved in memory tasks affected early by AD and other cognitive disorders, as described herein.

Particular embodiments of the subject matter described in this specification can be implemented to realize one or more of the following advantages. Essentially any number of study, study-test, test and delayed-test trials can be handled. Essentially any ordering of list items that may change across such trials can also be handled. Further, additional cognitive processes that permit different strengths of storage or retrieval within a given cognitive state can be included. Various numbers of list items from various types of recall tasks can be accommodated. Moreover, the models described can further incorporate storage parameters from delayed recognition or delayed cued recall tasks. The models described can address any cognitive, behavioral, affective, functional, sensory or motor task in which: (1) there are multiple trials in which a set of items are tested two or more times over some or all of these trials; and (2) a set of "states" and "process parameters" specified in the model characterize how they generate the item responses produced by subjects performing the cognitive, behavioral, affective, functional, sensory or motor task.

The details of one or more embodiments of the subject matter described in this specification are set forth in the accompanying drawings and the description below. Other features, aspects, and advantages of the invention will become apparent from the description, the drawings, and the claims.

BRIEF DESCRIPTION OF THE DRAWINGS

FIG. 5D shows a Four Trial Cognitive States Table.

FIG. 5E shows a Seven Trial Cognitive States Table.

DETAILED DESCRIPTION

Figure 1:
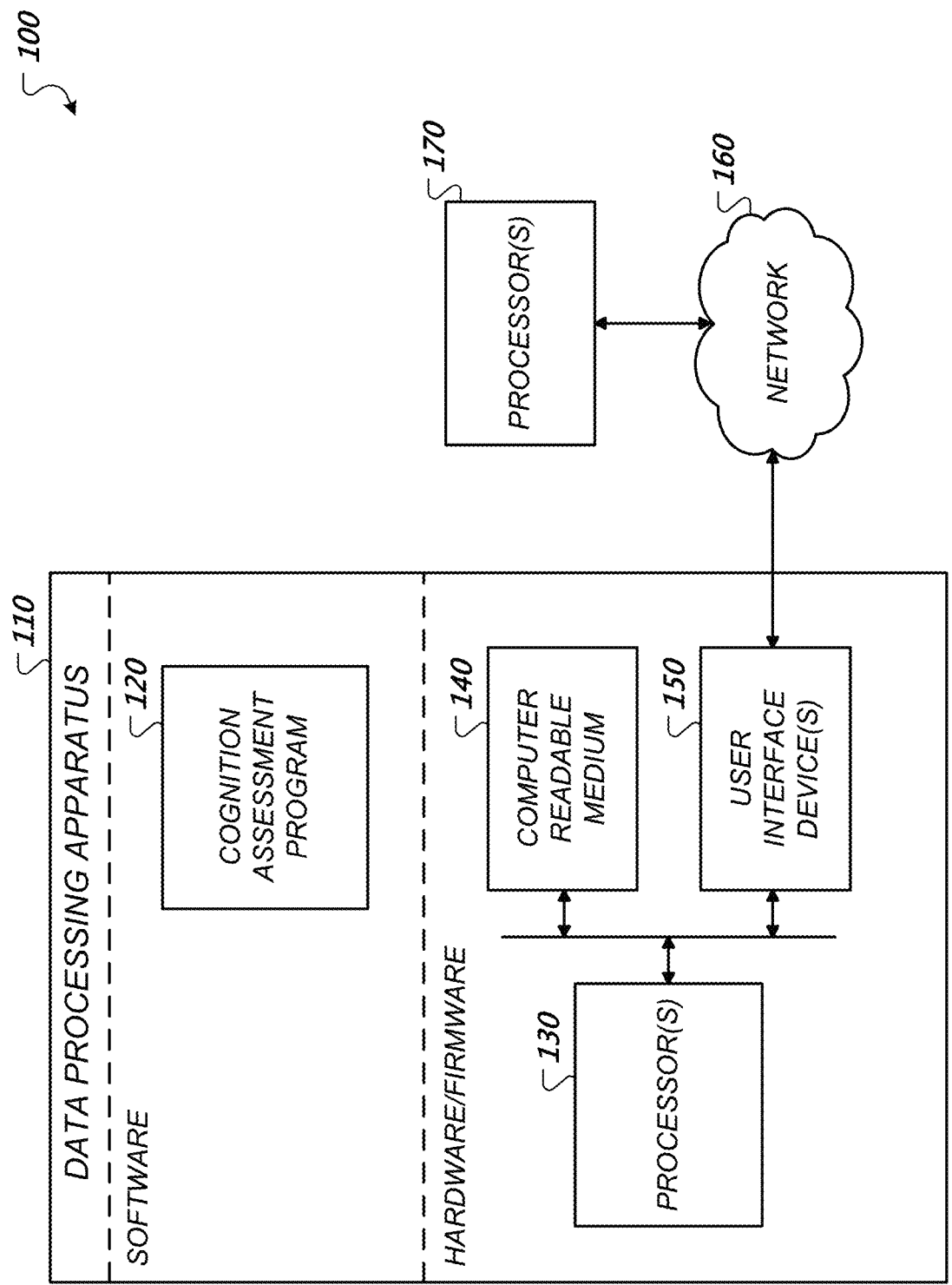
FIG. 1 shows an example of a system used to generate detailed cognition assessments.

FIG. 1 shows an example of a system 100 used to generate detailed cognition assessments. A data processing apparatus 110 can include hardware/firmware and one or more software programs, including a cognition assessment program 120. The cognition assessment program 120 operates in conjunction with the data processing apparatus 110 to effect various operations described in this specification. The program 120, in combination with the various hardware, firmware, and software components of the data processing apparatus, represent one or more structural components in the system, in which the algorithms described herein can be embodied.

The program 120 can be an application for determining and performing analysis on data collected to assess the cognition of a subject. A computer application refers to a computer program that the user perceives as a distinct computer tool used for a defined purpose. An application can be built entirely into an operating system or other operating environment, or it can have different components in different locations (e.g., a remote server). The program 120 can include or interface with other software such as database software, testing administration software, data analysis/computational software, and user interface software, to name a few examples. User interface software can operate over a network to interface with other processor(s). For example, the program 120 can include software methods for inputting and retrieving data associated with various recall tasks.

There are a number of recall tasks commonly used. These include, but are not limited to, the wordlist recall task of the AD Assessment Cognitive sub-scale (ADAS-Cog) test, the CERAD Wordlist memory task, the Auditory Verbal Learning Test (AVLT), Hopkins Verbal Learning Test, California Verbal Learning Test, the Free and Cued Selective Reminder Task, and the MCI Screen (MCIS) (available from Medical Care Corporation of Irvine, Calif.). In this document, the 10-item recall task of the ADAS-Cog from the AD Cooperative Study (ADCS), and the 15-item recall task of the AVLT from the Mayo Clinic Study on Aging (Mayo Aging) are used, but the systems and techniques described are applicable to other recall tasks and other recall tests, which can include various recall or recognition tasks.

The program 120 can effect various analytic processes of recall task data, which processes are described further below. The data processing apparatus includes one or more processors 130 and at least one computer-readable medium 140 (e.g., random access memory, storage device, etc.). The data processing apparatus 110 can also include one or more user interface devices 150. User interface devices can include display screen(s), keyboard(s), a mouse, stylus, modems or other networking hardware/firmware, etc., or any combination thereof. The subject matter described in this specification can also be used in conjunction with other input/output devices, such as a printer or scanner. The user interface device can be used to connect to a network 160, and can furthermore connect to a processor or processors 170 via the network 160 (e.g., the Internet).

Therefore, a user of the assessment program 120 does not need to be local, and may be connecting using a web browser on a personal computer or a tablet computer, or using other suitable hardware and software at a remote location. For example, a clinician at a testing center can access a web interface via the remote processor 170 in order to input test data for a given test. The test data can be the results of an already administered test, or the test data can be the information exchanged when actually administering the test using a network based testing system. In any event, data can be transmitted over the network 160 to/from the data processing apparatus 110. Furthermore the clinician can input test data and retrieve analysis based on that data or other data stored in a database. Note that the data processing apparatus 110 can itself be considered a user interface device (e.g., when the program 120 is delivered by processor(s) 170 as a web service).

Figure 2:
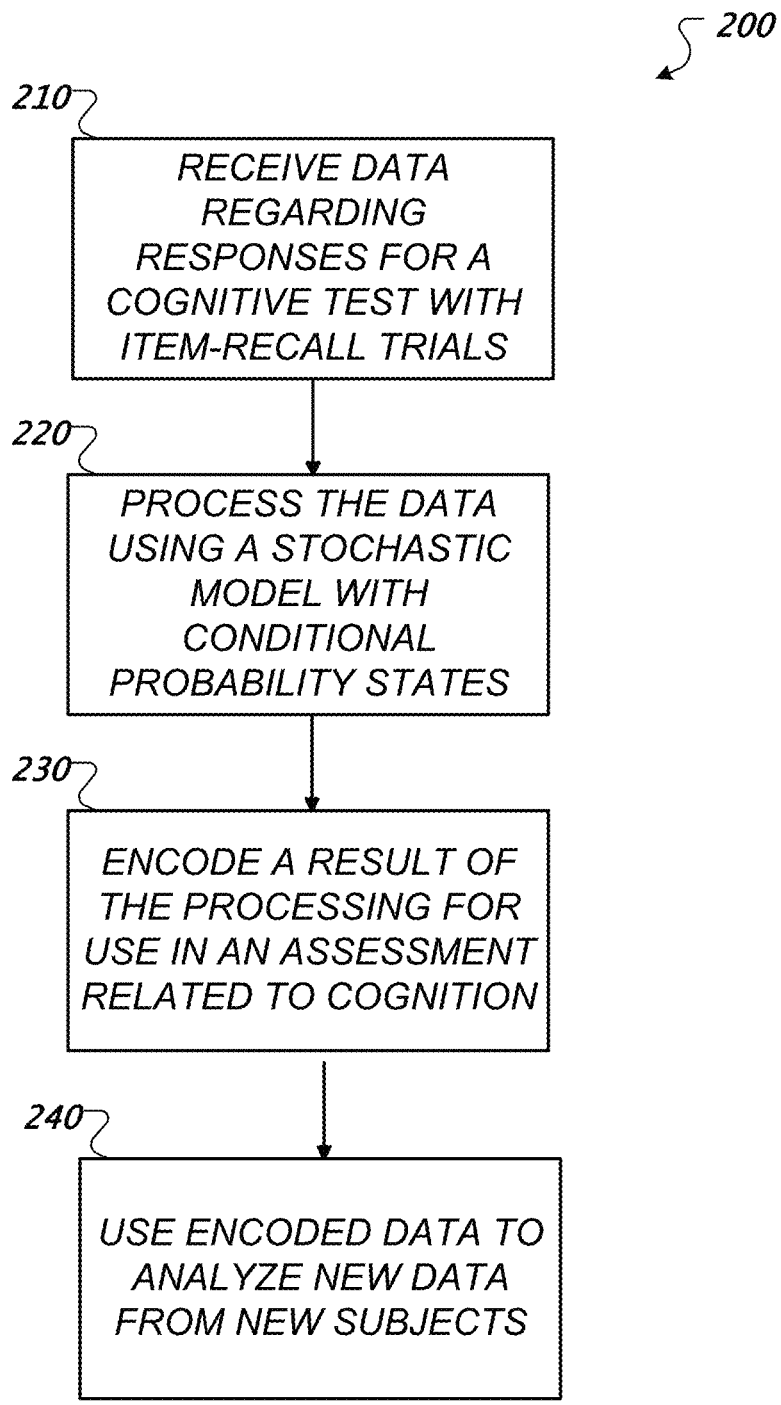
FIG. 2 shows an example of a process used to generate an analysis of data for a test of cognition.

FIG. 2 shows an example process 200 used to generate an analysis of data for a test of cognition. Data are received 210, where the data are regarding at least one person's responses, and lack thereof, for items of a cognitive test, where the cognitive test includes multiple item-recall trials used to assess cognition. As noted above, the information can include data from a previously administered test or from a test that is currently being administered. Nonetheless, the example process described in connection with FIG. 2, and other implementations of the more general concepts underlying this example process, are not practiced on the human body since such processes do not themselves involve an interaction necessitating the presence of the person.

The data can be received 210 from a database, a network or web-enabled device, a computer readable medium, or a standard input output device on a computer system, to name just a few examples. The multiple item-recall trials can include word recall tests of memory, or similar recall trials. In some implementations, the administered test includes the ADAS-Cog free recall task. In some implementations, the administered test includes the AVLT free recall task.

For the ADAS-Cog free recall task, there are three study-test trials and one delayed free recall test trial. Four wordlists were constructed for the ADAS-Cog free recall task, which have variable degrees of associability between all pairs of words in each list. The word presentation order is different for each study-test trial, but the pre-specified order of each study-test trial always remains the same for all subjects. After the third study-test trial, there is a delay of minutes, involving other unrelated tasks, after which the subject is given a delayed free recall test trial. For the ADCS ADAS-Cog recall task data, the wordlists used at each assessment did not vary across subjects, but different wordlists were used at different assessments.

For the AVLT free recall task, there are five study-test trials and two delayed free recall test trials. The Mayo Aging study used one wordlist and one distractor list for all subjects and all visits from 1987 to 2006. Associability varies over the possible pairs of the 15 list words. The same word presentation order is used over all five study-test trials. After the fifth study-test trial, the 15-item distracter wordlist is presented as a study-test trial, which takes approximately 5 minutes. The first delayed free recall test trial is then given, followed by performance of other unrelated tasks. At one hour after the fifth study-test trial, the seventh delayed free recall test trial is given.

As noted above, this document provides details with respect to implementations using the ADAS-Cog free recall task and the AVLT free recall task. However, the systems and techniques described are not limited to these specific arrangements of recall tasks. Other word lists (as well as other non-word based recall tasks) can be used. In some implementations, when word lists are used, the words in each word list can be linguistically and statistically equivalent. The words on each distinct list can have the same level of intra-list associability and usage frequency. Each list of words can have the same level of associability and usage frequency with each and every other list of words. The word lists can be used in different parts of a test (e.g., the distracter and learning word lists can be interchanged). Moreover, the words in each word list can be presented in the same order or different order.

The data are processed 220 using a stochastic model of a person's cognitive process, in which a conditional probability distribution of future states of the cognitive process depend only upon a present state. This can involve representing recall of an item in the multiple item-recall trials using distinct cognitive states and adjusting separate memory storage and retrieval parameters for each of the distinct cognitive states in the modeled cognitive process to account for position of the items in each respective trial of the multiple item-recall trials. The distinct cognitive states can include an unlearned state (U), an intermediate state (I), and a learned state (L). In addition, the processing at 220 can include computing a probability of a given item's response pattern using a set of all possible cognitive state sequences, minus some sequences that may be excluded based on the specific cognitive process model. For example, a proper subset of sequences that can be excluded based on the stochastic model of the cognitive process, such as excluding any sequences that transition from L to I or from I to U, or excluding any sequences that transition from L to I, from L to U, or from I to U.

In some implementations, the multiple item-recall trials can include at least one study trial and at least one non-study trial. In some cases, the number of trials can be determinable by an administrator, and in other cases, the number trials can be fixed. As will be appreciated, various trial set ups can be used, depending on the details of the implementation. In some implementations, the ADAS-Cog and AVLT recall trials can be used.

Although the ADAS-Cog and AVLT recall trials have been widely used, very little work has been done using their full, item recall data structure to quantify underlying cognitive processes of learning and memory. One reason that the ADAS-Cog free recall task has not been used for this purpose is that it uses a variable word order on each of its three study-test trials. This task design eliminates the possibility of obtaining a serial position curve on the subsequent test trials because of the changing study order of the words. A variable word order task design has hindered our knowledge of the latent cognitive processes involved in such free recall trials, and of how cognitively normal and MCI subject task performance differs.

In contrast to the ADAS-Cog, the AVLT free recall task uses a fixed word order that does not change across its five learning (study-test) trials, and uses a larger list of 15 items. This larger list of the AVLT requires more study-test trials than the ADAS-Cog in order to learn the items. The AVLT also has two delayed free recall trials at 5 minutes and at one hour, allowing the ability to measure decay in hippocampal memory. In contrast, the ADAS-Cog has just one delayed free recall trial at 5 minutes.

These substantive differences between ADAS-Cog and AVLT free recall tasks provide a good test of the generalizability of a memory model that predicts the item recall performance of either task. The memory model should be biologically realistic and consist of latent (not directly measurable) cognitive processes involved in memory task performance. The cognitive processes should have plausible scientific support that they exist in the brain and are implicated in memory task performance. The model should be robust in being able to predict a variety of memory tasks that are thought to use the cognitive processes specified by the model. The model should also be able to reliably predict memory task performance from different subject samples and populations. In one or more of the implementations of the systems and techniques described herein, all of these requirements can be satisfied.

In some implementations, the stochastic model used at 220 can be a hidden Markov model (HMM), as described in further detail below. In some implementations, at least two items of the multiple item-recall trials can be placed in different positions in separate administrations of individual trials of the multiple item-recall trials (e.g., as in the ADAS-Cog), and each of the memory storage and retrieval parameters can have an assigned subscript corresponding to an item's absolute position in a trial. Note that the items are not required to be placed in different positions, but rather are free to be placed in different positions, and the systems and techniques described herein can account for these different list positions placements using subscripts corresponding to absolute positions of items in a trial.

For example, the multiple item-recall trials can be three trials, and the subscripts can be x, y, and z, where x corresponds to the item's position in the first trial, y corresponds to the item's position in the second trial, and z corresponds to the item's position in the third trial. This is but one example, and the systems and techniques can employ as many subscripts as necessary for the test data received, where the subscripts correspond to the total number of multiple-item recall trials the subject is tested with or asked to study. In other words, the number of subscripts used can be adjusted according to the number of trials used, which can vary from implementation to implementation (e.g., based on the details of the cognitive test for which the implementation is designed), as well as within a given implementation (e.g., as determined by an administrator of the cognitive test).

In some implementations, the items of the multiple item-recall trials can have a fixed order that does not change across administrations of individual trials of the multiple item-recall trials (e.g., as in the AVLT free recall task). For example, the stochastic model can be an HMM, items of the multiple item-recall trials can have a fixed order that does not change across administrations of individual learning trials of the multiple item-recall trials. The systems and techniques described herein can be applied to such cognitive tests, as well as variations thereof. In general, the multiple item-recall trials can include one or more study trials and one or more non-study trials, where the study trial(s) can be learning trials having a fixed item order that does not change across the learning trials or learning trials having a variable item order that does change across the learning trials, and the non-study trial(s) can be free recall trials administered at respective different times after the learning trials. Data from one or more of such free recall trials can be used in combination with one or more additional parameters (of the memory storage and retrieval parameters) to measure decay in at least one memory state (e.g., hippocampal memory or pre-frontal memory) of the person.

Moreover, in some implementations, the processing at 220 can use a trial-dependent parameter for each of the storage and retrieval parameters for each of the distinct cognitive states in the modeled cognitive process to account for any non-stationary distribution of cognitive process parameters over the multiple item-recall trials. This can provide a mechanism to satisfy a core assumption of HMMs, which is that the distribution of each of the cognitive process parameters must be stationary over trials or time. In some cases (e.g., using ADAS-Cog), all of the cognitive process parameters may be stationary from trial one on. However, in other cases (e.g., using the AVLT, which has 15 items to learn), the cognitive process parameters may not have a stationary distribution from trial one on, and may take several trials to become stationary.

Nonetheless, this can be accounted for in the system. To make the cognitive process parameters stationary, it can be assumed that while the cognitive processing parameters are moving asymptotically towards having a stationary distribution with each study or study-test trial, their values are reduced by some proportion or factor, that is drawn from a uniform distribution on [0,1]. This proportion or factor is generally referred to herein as a "trial-dependent parameter", and such a trial-dependent parameter can be provided for each cognitive process parameter that is not stationary. This trial-dependent parameter can be engaged on each study-test trial until the parameter of the cognitive process becomes stationary, at which time the trial-dependent parameter can be discarded or ignored. As described in detail below, for the AVLT, it was found that it typically took two trials for the cognitive process parameters to reach a stationary distribution.

When the processing at 220 is complete (or concurrently with the processing at 220), the result of processing using the stochastic model can be encoded at 230, as needed, on a computer-readable medium to supply the result to a computer device for use in an assessment related to cognition. The encoding can employ any of various known techniques for saving data in physical memory devices and storage devices and systems for later retrieval (e.g., ASCII (American Standard Code for Information Interchange), HTML (HyperText Markup Language), XML (eXtensible Markup Language), records in a database system). The result can include a Boolean indication or a number, such as a measure of probability. Thus, the result represents intermediate information that has diagnostic or clinical relevance, which can be used by a doctor to make a diagnosis, or can be used as input to other processes and further assessment programs. Such further assessments can include computer programs that use the encoded data to analyze new data from new subjects at 240 and provide feedback and/or assessments of that new data. For example, the test of cognition can be administered one or more times to one or more additional people, and the response patterns from these additional administrations of the test can be compared with the encoded results to assist in early detection of MCI, as well as monitoring of disease progression, severity assessment and measurement of treatment effect.

Detailed examples of processes used to generate analyses of data for tests of cognition are now provided with reference to an ADCS sample and a Mayo Aging sample. For the ADCS sample, the ADAS-Cog wordlist memory task was administered to 724 subjects, of which 112 cognitively normal and 403 MCI subjects completed all assessments (every three months over three years). These subjects came from two studies of the ADCS. The 112 cognitively normal subjects met strict eligibility criteria, and the 403 amnestic MCI subjects were randomly assigned to placebo (N=132), donepezil (N=132), or Vitamin E (N=139), and completed all follow-up assessments.

For the Mayo Aging sample, the AVLT recall task was administered to 2,044 subjects from 1987 to 2006, for a total of 6,813 separate tests. 1,205 subjects entered the study as cognitively normal aging. 583 subjects were diagnosed with dementia due to AD, and 264 subjects were diagnosed with dementia due to Cerebrovascular Disease. All subjects received an extensive neuropsychologic test battery, MRI (Magnetic Resonance Imaging) of the brain, diagnostic laboratory testing, and were diagnosed by consensus of a panel of dementia experts. More recently, many subjects have had biomarkers studies of cerebrospinal fluid or amyloid PET (Positron Emission Tomography) scans. The Mayo Aging sample tested with the AVLT and analyzed for the present report included 178 normal aging subjects, and 131 AD subjects. The global Clinical Dementia Rating Score was 0 in 98% of normal aging subjects, 0.5 in 2%. 73% of AD subjects had MCI or mild dementia, and 27% had moderate to severe dementia.

Evalutating ADAS-Cog serial position effects: A phenomenon often observed in the behavioral measures of a standard free recall task is a U-shaped serial position curve where the recall probability of an item depends on its position in the study list. Generally, items presented at the beginning of the list and at the end of the list have a higher probability of being recalled. These effects are referred to as primacy and recency effects, respectively. Two cognitive processes are hypothesized to produce the primacy and recency effects. The primacy effect is hypothesized to be due to the additional time that items in the beginning of a list have available for encoding into short-term memory (i.e., hippocampal encoding). The recency effect is hypothesized to be due to items presented at the end of a list still residing in working memory (i.e., prefrontal cortex), even though they have had less time for encoding into short-term memory.

Figure 3A:
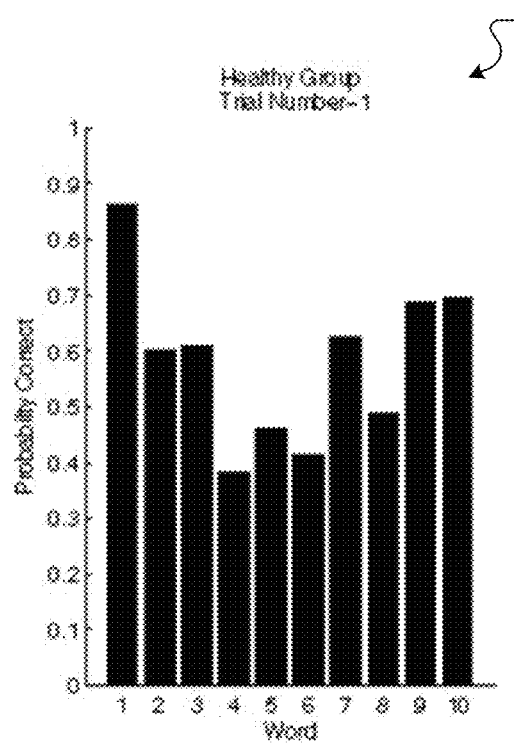
FIGS. 3A-3H show Alzheimer's Disease (AD) Assessment Cognitive sub-scale (ADAS-Cog) Serial Position Curves for the AD Cooperative Study (ADCS) Normal and mild cognitive impairment (MCI) Groups.
Figure 3B:
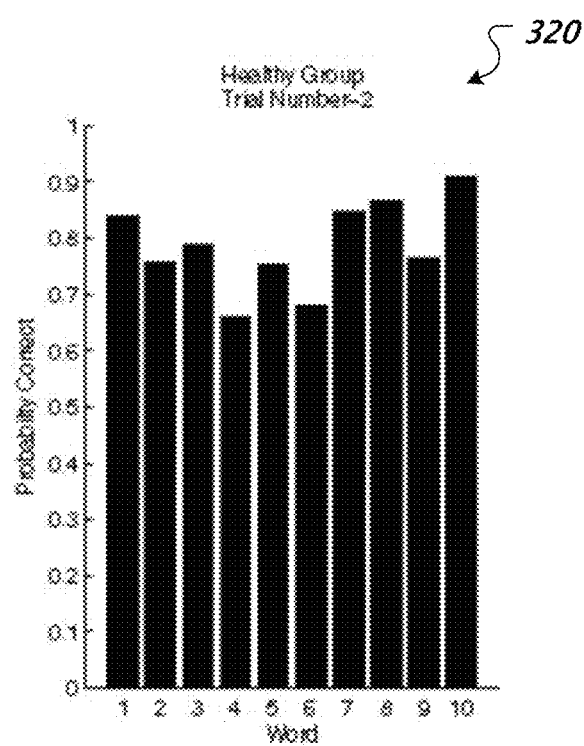
Figure 3C:
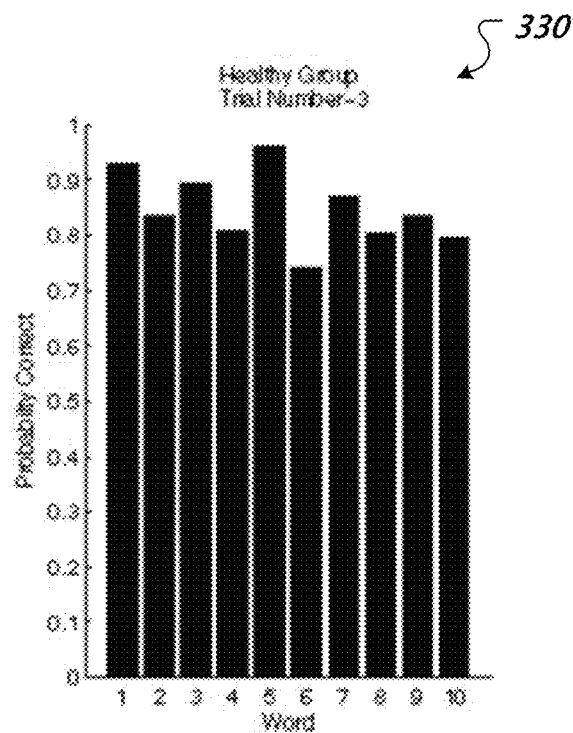
Figure 3D:
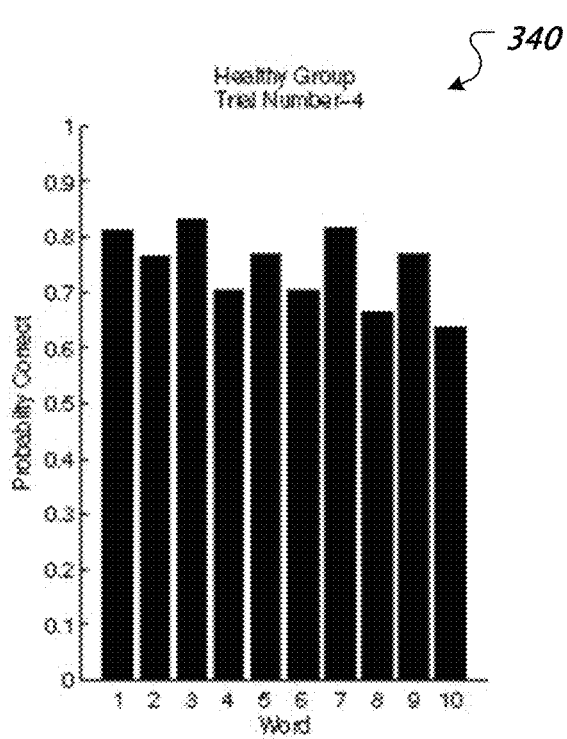

To examine the influence of a changing word order across learning (study) trials, the serial position curves of the ADCS ADAS-Cog free recall task data were generated. FIGS. 3A-3H show serial position curves over the four ADAS-Cog recall trials for the ADCS cognitively normal and MCI subjects. FIG. 3A shows a chart 310 of the probability of a correct answer, for each of the ten words, by the healthy group in trial number 1. FIG. 3B shows a chart 320 of the probability of a correct answer, for each of the ten words, by the healthy group in trial number 2. FIG. 3C shows a chart 330 of the probability of a correct answer, for each of the ten words, by the healthy group in trial number 3. FIG. 3D shows a chart 340 of the probability of a correct answer, for each of the ten words, by the healthy group in trial number 4.

Figure 3E:
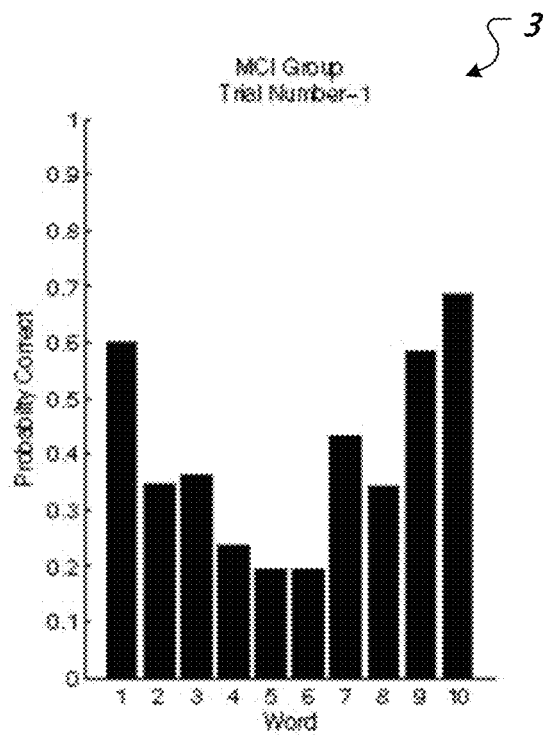
Figure 3F:
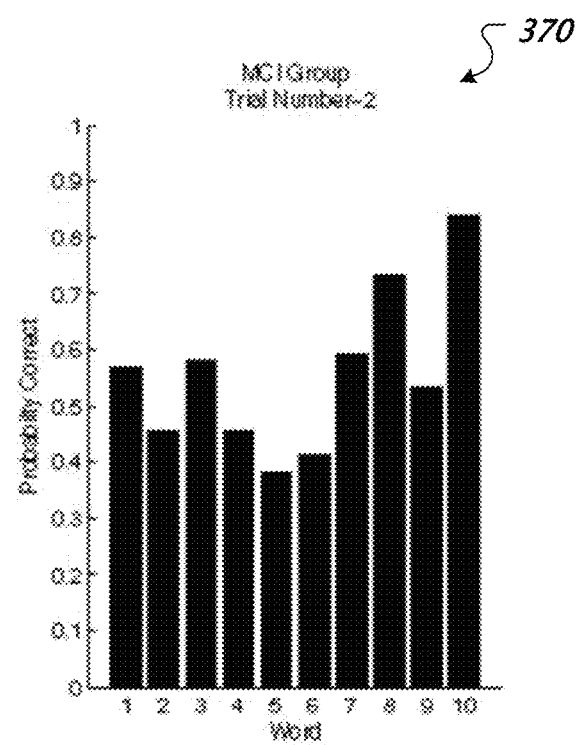
Figure 3G:
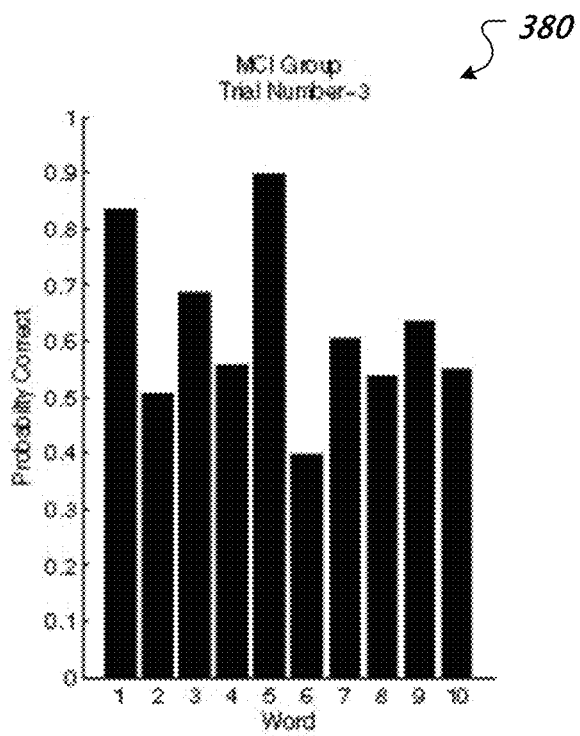
Figure 3H:
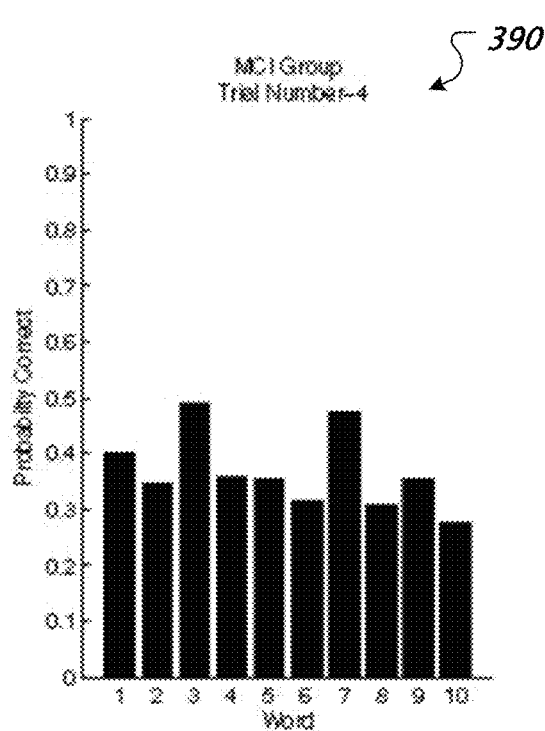

FIG. 3E shows a chart 360 of the probability of a correct answer, for each of the ten words, by the MCI group in trial number 1. FIG. 3F shows a chart 370 of the probability of a correct answer, for each of the ten words, by the MCI group in trial number 2. FIG. 3G shows a chart 380 of the probability of a correct answer, for each of the ten words, by the MCI group in trial number 3. FIG. 3H shows a chart 390 of the probability of a correct answer, for each of the ten words, by the MCI group in trial number 4.

For each recall trial and study group, the y-axis shows the percentage of subjects that correctly recalled a given list word. Note that for study-test trials 2 and 3 and the delayed recall test trial 4, the x-axis lists the words in the order they were presented in study trial 1, even though the word presentation order changed in study trials 2 and 3. When word presentation order does not change across study trials, the serial position effects of primacy and recency are demonstrated by a U-shaped appearance in recall probability, with earlier and later items recalled with higher probability. However, as shown in FIGS. 3A-3H, the changing word presentation order of the ADAS-Cog wordlist memory task across study trials alters this U-shaped appearance to some degree, and makes interpretation of the serial position effects more complex. For example, for the cognitively normal group, word 5 in study trial 3 has a higher probability of recall than word 1, which contradicts the expected recency effect if words were presented in the same order with each study trial. FIGS. 3A-3H therefore shows that the serial position curves for ADAS-Cog wordlist memory task do not lend themselves to straightforward interpretation of primacy and recency effects due to changing word order across study trials. To determine if there is useful information that can be extracted when word presentation order changes across study trials, a more sophisticated model of memory is needed.

In some implementations, a Hidden Markov Model (HMM) can be used, but other stochastic models are also possible. Traditional HMMs were developed for learning trials, such as those of paired-associate learning and free recall, dating back to early studies where cognitive structures and psychological processes were vital to the theoretical work of learning and memory. Using an HMM, learning can be represented as a function of storage and retrieval processes from latent cognitive states.

When such models were applied to item list memory experiments, the hypothesis was that the cognitive processes underlying task performance during these experiments were independently applied to each item, and were not influenced by the item's relationship to other list items in terms of adjacency, presentation order or associability. This hypothesis was not supported by these experiments, and gradually led to a reduction in the use of HMMs. These experiments found that the information lost in aggregating a trial's list items could not be overcome by adding more complex cognitive structures to the model.

In contrast, the HMM described herein is substantially different from earlier HMMs in that the present models can account for number of items, item position, item ordering across study trials, number of study trials, number of test trials, and the amount of learning that each cognitive process needs to reach a stable level of function (i.e., a stationary distribution) in modeling subject task performance.

Figure 4:
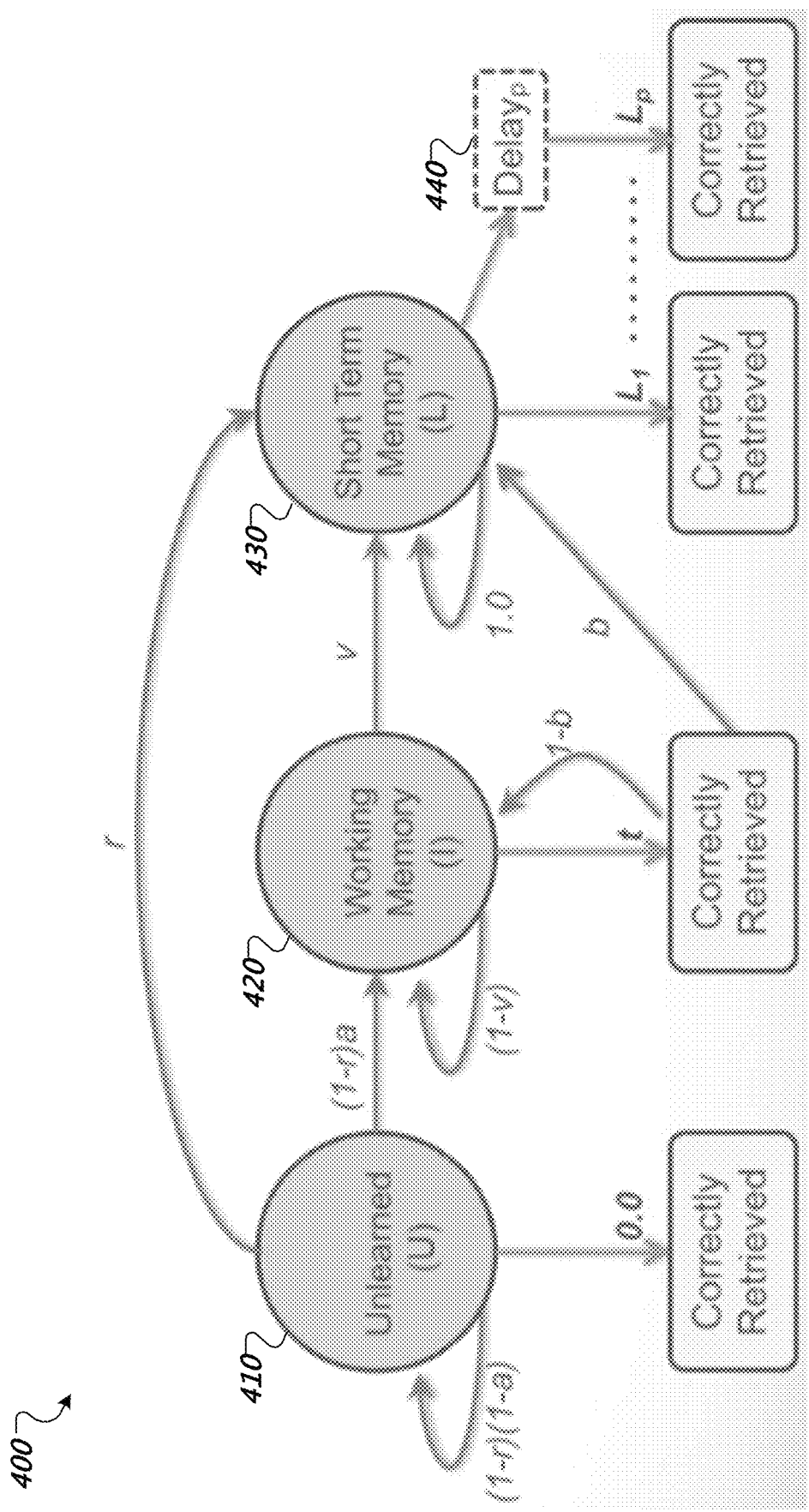
FIG. 4 shows a Hidden Markov Model (HMM) in accordance with various implementations of the systems and techniques described herein.

FIG. 4 shows an HMM 400 in accordance with various implementations of the systems and techniques described herein. The model assumes that any list item in any trial occupies one of three unobservable latent cognitive states. Each list item starts in the unlearned (U) state 410, which is the state where the subject has not encoded it. After each study trial, each list item can transition into another cognitive state with some probability depending on its list position. The second cognitive state 420, Intermediate state (I), corresponds to working memory (WM), which previous research has shown to be largely processed in the prefrontal cortex, and can typically store items for under one minute. The third state 430, Learned state (L), corresponds to short-term memory (STM), which previous research has shown to be largely processed in the hippocampus. STM takes several minutes to fully encode new information and can store the information for up to two weeks. Once an item has reached state L 430, it is hypothesized to remain there unless it is removed by decaying storage strength, as dictated by memory theory.

Arrows in FIG. 4 indicate transitions an item can make from the unobserved latent cognitive states—Unlearned, U; Intermediate or Working Memory (Prefrontal Cortex), I, and Learned or Short-Term Memory (Hippocampus), L. In addition, the model includes transitions reprsenting the chances of correctly retrieving the items from memory. There is zero chance of correctly retrieving an item from the Unlearned U state 410, and varying chances of recalling an item from the Intermediate I state 420 and the Learned L state 430. For the Intermediate I state 420, retrieving an item from memory has associated transitions to to either the Intermediate I state 420 or the Learned L state 430. For the Learned L state 430, there are varying chance of recalling the item depending on an amount time delay 440. The subscripts, $L_1, L_2, \ldots L_p$, represent the number of levels of decaying storage strength in L, when test trials or delayed test trials are given. The number of levels of decay is equal to or less than the number of test or delayed test trials.

Figure 5A:
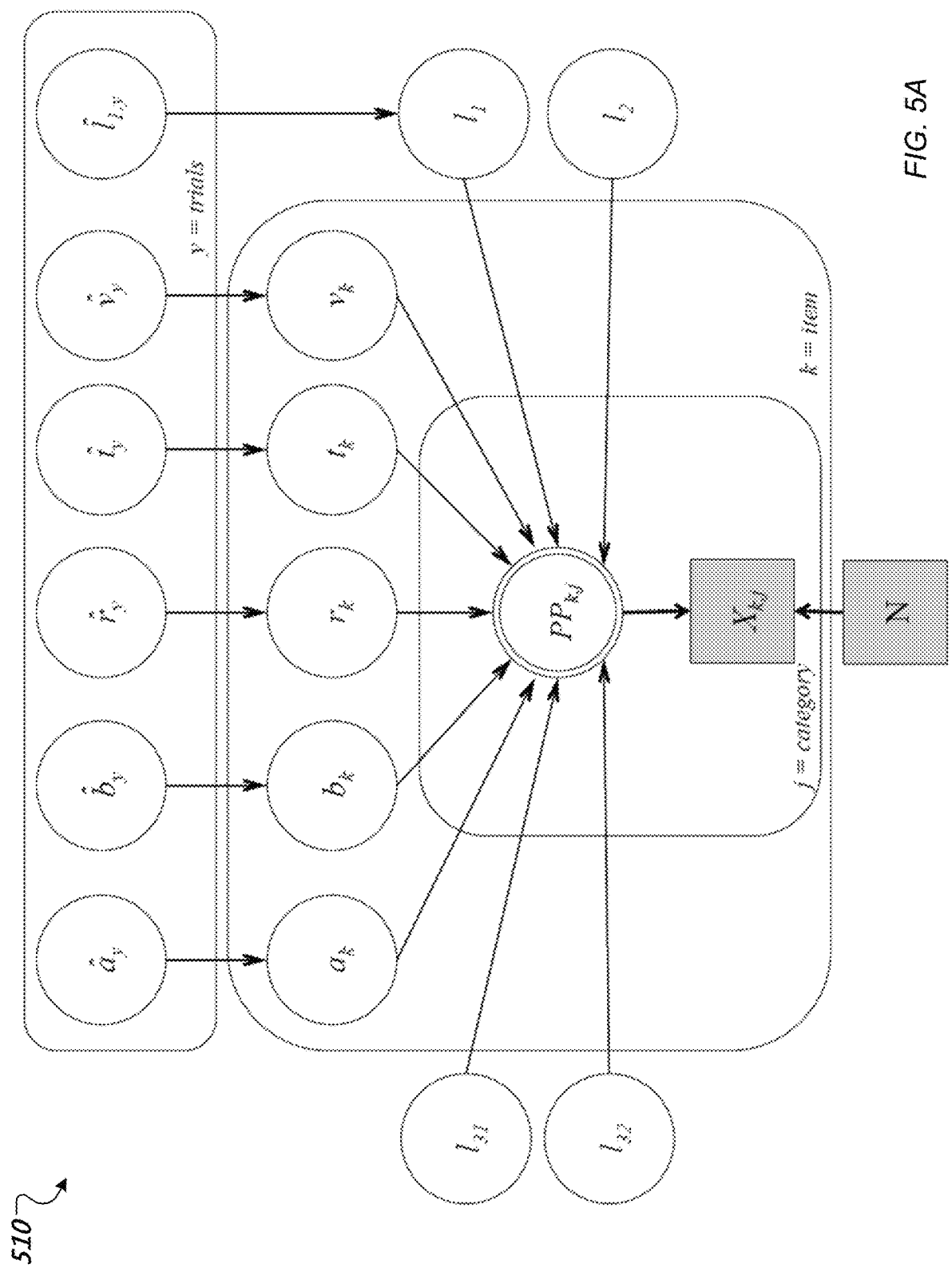
FIG. 5A shows an HMM in graphical form for a model with two strengths of storage for recall from state, L, during the study-test trials, and two strengths of storage for recall from state, L, during the delayed test trials, and including trial-dependent parameters.

FIG. 5A shows an HMM in graphical form for a model with two strengths of storage for recall from state, L, during the study-test trials ($l_1$, $l_{31}$), and two strengths of storage for recall from state, L, during the delayed test trials ($l_2$, $l_{32}$), and including trial-dependent parameters denoted by $\hat{a}$ over the letter. The square $X_{k,j}$ corresponds to the number of observed 4-tuple responses for response pattern (or category), j, for item, k. The total number of response patterns of any given item, k, correspond to the number of patterns of recalling item, k, given the number of trials in the recall task. For the ADAS-Cog recall task, there are four recall trials so there are $2^4=16$ possible response patterns for each item, k. For example, one response pattern for any given item, k, of the ADAS-Cog recall task, is {0010}, in which a subject recalls the item only on the third trial. For the AVLT recall task, there are seven recall trials, so there are $2^7=128$ response patterns for each item, k. The double ringed circle, $PP_{k,j}$ corresponds to the HMM's generated prediction of $X_{k,j}$. The cognitive process parameters are $a_k$, $b_k$, $r_k$, $t_k$, $v_k$, $l_1$, $l_2$, $l_{31}$, or $l_{32}$. The cognitive processes that each of the parameters perform are specified in FIG. 4.

The cognitive processes inside the plate, k=Item, have parameters, $a_k$, $b_k$, $r_k$, $t_k$, and $v_k$ for each item, k, and are denoted by the open circles with a single ring about them. The cognitive process parameters from state, L ($l_1$, $l_2$, $l_{31}$, or $l_{32}$) are outside the plate, k=Item, and have one parameter each. Parameters, $l_1$ and $l_{31}$, represent the process of items transferring into state, L, during study or study-test trials, and being retrieved from state, L, during the study-test trials. Parameters, $l_2$ and $l_{32}$, represent the process of items stored in state, L, that are retrieved during test trials. Although FIG. 5A shows four retrieval processes from state, L, the number of retrieval processes will vary according to the HMM constructed. For example, the AVLT recall task uses all four of these retrieval state parameters ($l_1$, $l_2$, $l_{31}$, $l_{32}$) with $l_2$ and $l_{32}$ corresponding to retrieval from the AVLT's delayed free recall tasks at 5 minutes and one hour after study-test trial 5. However, the ADAS-Cog recall task only uses the $l_1$ and $l_2$ retrieval parameters for state, L, with $l_2$ corresponding to retrieval from the ADAS-Cog's delayed free recall tasks at 5 minutes. For implementations with different numbers and types of trials, different numbers of corresponding retrieval processes can be included in the HMM. In various implementations, the HMM can accommodate different degrees of decay from state, L, by adding additional parameters that measure state, L, storage or retrieval strength.

Furthermore, the extension of the HMM that permits substantial flexibility in handling a variety of recall tasks and models is the incorporation of trial-dependent parameters, which can guarantee that the model will achieve stationary distributions of its cognitive process parameters. In the example HMM 510, the trial-dependent parameters are $\hat{a}_y$ to $\hat{l}_{1,y}$, which are each assigned to one cognitive process parameter. The trial-dependent parameters are used to satisfy the HMM assumption of a stationary distribution for each cognitive process parameter that may be changing over study-test trials. Each trial-dependent parameter is distributed between [0,1] and associated with a study trial of a corresponding model (cognitive process) parameter. For each study trial, a value is drawn from the ancillary trial-dependent parameter's distribution, and multiplied with the cognitive process parameter. The multiplicative product reduces the value of the cognitive process parameter for that trial. Once the trial-dependent parameters reach a stable value over successive trials, it no longer needs to be multiplied with the cognitive process parameter. The core assumption of the HMM is then satisfied. One can then use that trial-dependent parameter on the number of study trials needed for the cognitive process parameter to satisfy the stationary distribution assumption of the HMM.

Phenomenologically, the trial-dependent parameters replicate what occurs when subjects attempt to learn larger lists of items. Subjects require more study trials to learn them, such that their performance is non-stationary until the underlying cognitive processes have adjusted to accommodate the larger number of items.

During a study trial, the model hypothesizes that an item in state, U, can transition into either state, I, via storage parameter, a, or state, L, via storage parameter, r, or remain in state, U. If an item enters state, I, the model hypothesizes that it remains there unless another exposure of the same item transitions it into state, L. This transition can occur in two ways: 1) with exposure of the same item on any subsequent study trial (storage parameter, v); or 2) with recall of that item on the test portion of a study-test trial (storage parameter, b). Support for the existence of storage parameter, v, comes from past research demonstrating recall of items on test trials that were not recalled during study-test trials. For example, if the item, "butter", is stored in state, I, and is not recalled on any of the study-test trials, but is recalled on a subsequent delayed recall test trial, then it entered state, L, during one of the study-test trials via storage parameter, v. The model in FIG. 4 also hypothesizes that items entering the learned state, L, remain there without further transitions into other states. However, the cognitive process parameters, $L_1$, $L_2$, . . . $L_p$, allow the L state's strength of storage, or retrieval, to decay over time, which is evaluated by subsequent test or delayed test trials. As specified in the model shown, the HMM provides the option of incorporating cognitive processes that transfer items into state, L, during study or study-test trials (e.g., $l_1$, $l_{31}$) such that they could be transferred into any of the levels of strength in state, L, which are represented by those $L_p$ parameters that retrieve items only during test or delayed test trials.

HMM Instantiation for the ADAS-Cog and AVLT Recall Tasks: The ADAS-Cog model contains seven cognitive process parameters: four for storage, which are r, a, v, and b, and three for retrieval, which are t, $L_1$, and $L_2$. The ADAS-Cog HMM instantiation did not require the use of trial-dependent parameters because its cognitive processes had stationary parameter distributions from the first study-test trial onward. The AVLT model contains the same cognitive process parameters as the ADAS-Cog model, but also contains additional retrieval parameters, $l_{31}$ and $l_{32}$, and the aforementioned trial-dependent parameters to assure asymptotic movement to stationary parameter distributions.

From the Unlearned State, U, an item can remain there, transition into state, I, or transition into state, L. The storage parameter, r, represents the probability that an item transitions from state, U, to state, L. The storage parameter, a, represents transition from state, U, to state, I. However, an item can only do this if it did not transition from state, U, into state, L. Therefore, the probability of transitioning from state, U, to state, I=(1−r)(a). If an item remains in state, U, then it does so with probability (1−r)(1−a).

From Intermediate State, I, during a study trial, an item can transition into state, L, with probability, v, (the I to L storage parameter), or remain in state, I, with probability, 1−v. Also, from state, I, if an item is correctly recalled during the test trial part of a study-test trial, it can transition into state, L, with probability, b, or if not recalled, remain in state, I, with probability, 1−b.

During the study-test trials, each item is either in state U, I or L. Retrieval from each of these states during the test trial portion of a study-test trial is specified by a retrieval parameter. Items cannot be retrieved from the Unlearned state, U, but can be retrieved from the I state with probability, t, and can be retrieved from the Learned state, L, with probability, Ii. There is also the possibility that, during a study-test trial, an item can transfer into state, L, and have weaker storage strength than occurred with $l_1$. The ADAS-Cog HMM need not allow this possibility, but the AVLT HMM does, via parameter, $l_{31}$. These item retrieval probabilities from each of these cognitive states during the test part of a study-test trial are as follows:

$Pr$(correct recall|$U$ State, study-test trial)=0

$Pr$(correct recall|$I$ State, study-test trial)=$t$ $Pr$(correct recall|$L$ State, first strength level, study-test trial)=$l_1$ $Pr$(correct recall|$L$ State, second strength level, study-test trial)=$l_{31}$ After the study-test trials, if a delay occurs before another test trial, the strength of memory storage in the state, L, can decay.

Items in states, U or I, have zero probability of being recalled in any delayed recall test trial. However, the retrieval parameter, $l_2$, retrieves items from state, L, at the first level of storage strength, which is accessed at least by the first delayed recall test trial. Items in state, L, have probability, $l_2$, of being retrieved in the first delayed recall test trial. Both the ADAS-Cog and AVLT HMM instantiations have an $l_2$ parameter. In addition, the AVLT HMM has a weaker level of storage strength in state, L, represented by the $l_3$ parameters, $l_{31}$ and $l_{32}$. As previously discussed, via parameter, $l_{31}$, during study-test trials, items can be stored more weakly into state, L, and retrieved. But items can also be retrieved from this weaker state of L, during delayed test trials via parameter, $l_{32}$. The probabilities of retrieving an item from each of these states during delayed recall test trials are as follows:

$Pr$(correct recall|$U$ State, delayed free recall test trial)=0

$Pr$(correct recall|$I$ State, delayed free recall test trial)=0

$Pr$(correct recall|$L$ State, first delayed free recall test trial)=$l_2$ $Pr$(correct recall|$L$ State, second delayed free recall test trial)=$l_{32}$ As previously stated, many HMMs for learning are rarely in use today because of the assumption that the storage and retrieval parameters are the same for all items in the list, and because these parameters are not influenced by item order across study-test trials. The present disclosure has extended the HMM by adjusting the storage and retrieval parameters to account for the list position of each item in each study trial. This adjustment can be accomplished by assigning subscripts, for each study or study-test trial, to the storage parameters, r, a, v and b, and to the retrieval parameters, t. Note that after examining the effects of item list position for each of these parameters, we did not see substantial variability for the $l_1$ or $l_2$ parameters. We therefore did not estimate separate $l_1$ or $l_2$ parameters for each item list position in the final model. For the ADAS-Cog HMM instantiation, these subscripts indicate the position of a given item in the three study trials—subscript, x, corresponds to the item's position in the first study trial; subscript, y, corresponds to the item's position in the second study trial; subscript, z, corresponds to the item's position in the third study trial. Any number of study or study-test trials can be used, and the number of subscripts adjusted accordingly.

These cognitive states are analogous to different brain areas involved in memory storage and retrieval, which have different temporal processing characteristics that are expressed in the differences in storage and retrieval parameters assigned to these cognitive states. These differences from the prior approach are substantive, biological and innovative. They also allow the extraction of useful information from a large number of wordlist memory tasks in which items can be ordered in any possible presentation arrangement across study trials. Examples of such list memory tasks include those of the ADAS-Cog, the CERAD battery, the Auditory Verbal Learning Task (VLT), the California VLT, the Hopkins VLT, the Buschke-Fuld Cued Selective Reminding Task, the MCI Screen and many others.

To summarize, we have extended the machinery of the HMMs by allowing the storage and retrieval parameters to be different for each list position. This implies that when an item appears in position, k, on a study trial, the parameters that govern the state transitions and recall probabilities depend on position, k. Thus unless restrictions are placed, there are "n" values of each parameter (one for each list item or list position). The extended HMM also accommodates any number of study and test trials, plus allows each cognitive process parameter to have trial-dependent parameters that account for the number of study or study-test trials required to achieve a stationary distribution, which is when the trial-dependent parameter reaches a steady value.

Detailed examples of data and model equations are now provided. For the ADAS-Cog free recall task there are item response patterns over 4 trials. For four recall trials, the number of possible response patterns of recalling or not recalling a given word is $2^4=16$. For example, if a subject does not recall the word, butter, in any of the four trials, then butter's response pattern is (0000). If a subject recalls butter in all four trials, then butter's response pattern is (1111). Aggregating each item's response patterns over subjects gives the frequency counts that provide the basis for estimating the model's storage and retrieval parameters.

As discussed above, the model's three cognitive states—U, I, or L—for any given trial are not directly observable (hence the name, Hidden Markov model). After each study or test trial, any given item will reside in one of these states. To compute the probability of any given item's response pattern, one adds the probabilities of each possible sequence of the cognitive states that can occur over the 4 trials for this item's response pattern. Table 1 shows an example of how to compute the probability of an item's response pattern, 0010, in which the item was only recalled on the third study-test trial.

TABLE 1

Probability Computation for the 0010 Response Pattern

| | | | | | Subject's Response Pattern | | | |
|---|---|---|---|---|---|---|---|---|
| | | | | | 0 | 0 | 1 | 0 |
| Cognitive State Sequence | | | | | Probabilty of (State \| Trial #, Response Pattern, Model) | | | |
| Trial Number | | | | Study-Test | Study-Test | Study-Test | Delayed | |
| 1 | 2 | 3 | 4 | Trial 1 | Trial 2 | Trial 3 | Test Trial 4 | |
| U | U | U | U | | | | | |
| U | U | I | U | $(1-r_x)(1-a_x)$ | $(1-r_y)(1-a_y)$ | $(1-r_z)a_zt_z(1-b_z)$ | | |
| U | U | L | L | $(1-r_x)(1-a_x)$ | $(1-r_y)(1-a_y)$ | $r_zL_1$ | $1-L_2$ | |
| U | U | *L | L | $(1-r_x)(1-a_x)$ | $(1-r_y)(1-a_y)$ | $(1-r_z)a_zt_zb_z$ | $1-L_2$ | |
| U | I | I | | $(1-r_x)(1-a_x)$ | $(1-r_y)(a_y)(1-t_y)$ | $(1-v_z)t_z(1-b_z)$ | | |
| U | I | *L | L | $(1-r_x)(1-a_x)$ | $(1-r_y)(a_y)(1-t_y)$ | $(1-v_z)t_zb_z$ | $1-L_2$ | |
| U | I | L | L | $(1-r_x)(1-a_x)$ | $(1-r_y)(a_y)(1-t_y)$ | $v_zL_1$ | $1-L_2$ | |
| U | L | L | L | $(1-r_x)(1-a_x)$ | $r_y(1-L_1)$ | $L_1$ | $1-L_2$ | |
| U | *L | L | L | $(1-r_x)(1-a_x)$ | | | | |
| I | I | I | | $(1-r_x)a_x(1-t_x)$ | $(1-v_y)(1-t_y)$ | $(1-v_z)t_z(1-b_z)$ | | |
| I | I | *L | L | $(1-r_x)a_x(1-t_x)$ | $(1-v_y)(1-t_y)$ | $(1-v_z)t_zb_z$ | $1-L_2$ | |
| I | I | L | L | $(1-r_x)a_x(1-t_x)$ | $(1-v_y)(1-t_y)$ | $v_zL_1$ | $1-L_2$ | |
| I | L | L | L | $(1-r_x)a_x(1-t_x)$ | $v_y(1-L_1)$ | $L_1$ | $1-L_2$ | |
| L | L | L | L | $r_x(1-L_1)$ | $1-L_1$ | $L_1$ | $1-L_2$ | |
| *L | L | L | L | | | | | |

Table 1 above shows an example of how to compute the probability of the response pattern 0010 for a given item, which is recalled only on the third study-test trial. The rows of Table 1 list each sequence of cognitive states that are given in the Four Trial Cognitive States Table 2 in FIG. 5D. For the response pattern, 0010, the cognitive state sequence, UUUU, has zero probability because an item cannot be recalled from the Unlearned state, U, in Trial 3. The second cognitive state sequence, UUI, is possible because the item can be recalled from state, I, in trial 3. The probability of each cognitive state for the response pattern, 0010, of a given item, is shown in the rows to the right of the cognitive state sequence. Cognitive state sequences that are not possible for the given response pattern have no formulae under the Study-Test and Delayed Test Trial columns. The storage and retrieval parameter strengths or probabilities are determined by the given response pattern, the specific cognitive state sequence used, and the positions of each list item in the study trials. Reverse state transitions are not allowed (i.e., no transitions from I to U, L to I or L to U).

To determine how to compute a given response pattern, e.g., in the case of using the ADAS-Cog wordlist memory recall task, the following method can be used for a wordlist or item list memory recall task. At the beginning of the test, all items start in the unlearned state, U. For study trial 1, an item can remain in state U, or transition to be stored in states I or L as determined by storage parameters, a and r respectively. For test trial 1, the retrieval parameter is t if an item was stored in state I, and is $L_1$ if an item was stored in state, L. If an item is correctly recalled from state I during test trial 1, then it can transition to be stored in state L according to the parameter, b, or remain in state I with probability 1−b.

These parameters are further adjusted according to the given item's list position in study trial 1, which is given by the subscript, x. For study trial 2, an item can remain in its previous state, or transition to a more learned state. For example, if the item was in state I during study trial 2, it could remain in state I with probability, 1−v, or transition to state L with probability, v. For test trial 2, the retrieval parameter is t if an item was stored in state I, and is $L_1$ if an item was stored in state, L. If an item is correctly recalled from state I during test trial 2, then it can transition to be stored in state L according to the parameter, b, or remain in state I with probability 1−b. These parameters are further adjusted according to the given item's list position in study trial 2, which is given by the subscript, y. For study trial 3, the item can remain in its previous state, or transition to a more learned state. For test trial 3, the retrieval parameter is t if an item was stored in state I, and is $L_1$ if an item was stored in state, L. If an item is correctly recalled from state I during test trial 3, then it can transition to be stored in state L according to the parameter, b, or remain in state I with probability 1−b. These parameters are further adjusted according to the given item's list position in study trial 3, which is given by the subscript, z. For delayed recall test trial 4, if the item is in state U or I, it cannot be retrieved (probability of recall=0). If the item is in state L, then it can be recalled with probability $L_2$, which reduces the memory storage strength in state L as a function of the delay.

The Four Trial Cognitive States Table 2 in FIG. 5D shows the possible cognitive state sequences for a given pattern of responses for a given list item in a four trial recall task with three study-test trials and one delayed test trial. The Hidden Markov Model here consists of three latent cognitive states. U: Unlearned state. I: Intermediate state. L: Learned state. The cognitive state in each column indicates the state the item is in at the conclusion of that trial. Note that not all cognitive state sequences are possible for any given pattern of item responses.

During the study-test trials, if a given item is correctly recalled from state, I, during the test part of the study-test trial, it can transfer it into the learned state, L, via cognitive process, b. Note that if, on the previous trial, the item was in state, U, it can still transfer into state, L, via cognitive process, b, during the test part of the current study-test trial, because the item could have transferred from state U, to I, during the study part of the current study-test trial. A given item can also transfer into state, L, during the study part of the study-test trial, via cognitive process, r, if the item was in state, U, on the previous trial, or via cognitive process, v, if the item was in state, I, on the previous trial. The cognitive state sequences that have two ways of being transferred into state, L, have state, L, and the previous state, U or I, highlighted with bold text and double borders in Table 2 in FIG. 5D.

Example: Calculating a Cognitive State Sequence, UUI, for Response Pattern {0010}. To illustrate how a specific cognitive state sequence in Table 1 is calculated for a given item's response pattern of 0010, consider the cognitive state sequence, UUI in the second cognitive state sequence row. For study-test trial 1, the item is in list position, x, is not recalled, and remains in state U with probability $(1-r_x)(1-a_x)$. For study-test trial 2, the item is in list position, y, is not recalled and remains in state U with probability $(1-r_y)(1-a_y)$. For study-test trial 3, the item is in list position, z, is recalled, and transitions to the working memory state, I, with probability, $(1-r_z)a_zt_z(1-b_z)$. For delayed test trial 4, the item cannot be recalled because it was in state, I, after study-test trial 3. The probability of the given item's response pattern of 0010 for the cognitive state sequence, UUI, is then determined by taking the product of the probabilities of these trials.

For a given item's response pattern, the probabilities of each of the possible cognitive state sequences for that response pattern are then summed together to compute the probability of the given item's response pattern, given the model. Table 2 in FIG. 5D lists the possible cognitive state sequences for a four-trial multiple item-recall task, in which each list item is coded as either recalled or not recalled.

Presented now are the formulae for computing the probabilities of each of the 16 possible response patterns—0000 to 1111—given a particular list item and the present HMM. For each of a given item's 16 possible response patterns, the formulae show the probability calculations for the possible cognitive state sequences allowable for that response pattern:

$$Pr(0000 \mid M) = [(1-L_1)^3(1-L_2)r_x +$$
$$(1-r_x)a_x(1-t_x)v_y(1-L_1)^2(1-L_2) +$$
$$(1-r_x)a_x(1-t_x)(1-v_y)(1-t_y)v_z(1-L_1)(1-L_2) +$$
$$(1-r_x)(1-a_x)r_y(1-L_1)^2(1-L_2) +$$
$$(1-r_x)(1-a_x)(1-r_y)a_y(1-t_y)v_z(1-L_1)(1-L_2) +$$
$$(1-r_x)(1-a_x)a_y(1-t_y)(1-v_z)(1-t_z) +$$
$$(1-r_x)(1-a_x)(1-r_y)(1-a_y)(1-r_z)(1-a_z) +$$
$$(1-r_x)(1-a_x)(1-r_y)(1-a_y)(1-r_z)a_z(1-t_z) +$$
$$(1-r_x)a_x(1-t_x)(1-v_y)(1-t_y)(1-v_z)(1-t_z) +$$
$$(1-r_x)(1-a_x)(1-r_y)(1-a_y)r_z(1-L_1)(1-L_2)]$$

$$Pr(0010 \mid M) = [(1-L_1)^2L_1(1-L_2)r_x + (1-r_x)a_x(1-t_x)v_y(1-L_1)$$
$$L_1(1-L_2) + (1-r_x)a_x(1-t_x)(1-v_y)(1-t_y)v_zL_1(1-L_2) +$$
$$(1-r_x)a_x(1-t_x)(1-v_y)(1-t_y)(1-v_z)t_zb_z(1-L_2) +$$
$$(1-r_x)(1-a_x)r_y(1-L_1)L_1(1-L_2) +$$
$$(1-r_x)(1-a_x)(1-r_y)a_y(1-t_y)v_zL_1(1-L_2) +$$
$$(1-r_x)(1-a_x)(1-r_y)a_y(1-t_y)(1-v_z)t_zb_z(1-L_2) +$$
$$(1-r_x)(1-a_x)(1-r_y)a_y(1-t_y)(1-v_z)t_z(1-b_z) +$$
$$(1-r_x)(1-a_x)(1-r_y)(1-a_y)(1-r_z)a_zt_z(1-b_z) +$$
$$(1-r_x)a_x(1-t_x)(1-v_y)(1-t_y)(1-v_z)t_z(1-b_z) +$$
$$(1-r_x)(1-a_x)(1-r_y)(1-a_y)r_zL_1(1-L_2) +$$
$$(1-r_x)(1-a_x)(1-r_y)(1-a_y)(1-r_z)a_zt_zb_z(1-L_2)]$$

$$Pr(0100 \mid M) = [(1-L_1)^2L_1(1-L_2)r_x + (1-r_x)a_x(1-t_x)v_yL_1(1-L_1)$$
$$(1-L_2) + (1-r_x)a_x(1-t_x)(1-v_y)t_yb_y(1-L_1)(1-L_2) +$$
$$(1-r_x)a_x(1-t_x)(1-v_y)t_y(1-b_y)v_z(1-L_1)(1-L_2) +$$
$$(1-r_x)(1-a_x)r_yL_1(1-L_1)(1-L_2) +$$
$$(1-r_x)(1-a_x)(1-r_y)a_yt_yb_y(1-L_1)(1-L_2) +$$
$$(1-r_x)(1-a_x)(1-r_y)a_yt_y(1-b_y)v_z(1-L_1)(1-L_2) +$$
$$(1-r_x)(1-a_x)(1-r_y)a_yt_y(1-b_y)(1-v_z)(1-t_z) +$$
$$(1-r_x)a_x(1-t_x)(1-v_y)t_y(1-b_y)(1-v_z)(1-t_z)]$$

$$Pr(0110 \mid M) = [(1-L_1)L_1^2(1-L_2)r_x + (1-r_x)a_x(1-t_x)v_yL_1^2(1-L_2) +$$
$$(1-r_x)a_x(1-t_x)(1-v_y)t_yb_yL_1(1-L_2) +$$
$$(1-r_x)a_x(1-t_x)(1-v_y)t_y(1-b_y)v_zL_1(1-L_2) +$$
$$(1-r_x)a_x(1-t_x)(1-v_y)t_y(1-b_y)(1-v_z)t_zb_z(1-L_2) +$$
$$(1-r_x)(1-a_x)r_yL_1^2(1-L_2) + (1-r_x)(1-a_x)(1-r_y)a_yt_yb_y$$
$$L_1(1-L_2) + (1-r_x)(1-a_x)(1-r_y)a_yt_y(1-b_y)v_xL_1(1-L_2) +$$
$$(1-r_x)(1-a_x)(1-r_y)a_yt_y(1-b_y)(1-v_z)t_zb_z(1-L_2) +$$
$$(1-r_x)(1-a_x)(1-r_y)a_yt_y(1-b_y)(1-v_z)t_z(1-b_z) +$$
$$(1-r_x)a_x(1-t_x)(1-v_y)t_y(1-b_y)(1-v_z)t_z(1-b_z)]$$

$$Pr(0001 \mid M) = [(1-L_1)^3L_2r_x + (1-r_x)a_x(1-t_x)v_y(1-L_1)^2L_2 + (1-r_x)$$
$$(1-v_y)(1-t_y)v_z(1-L_1)L_2 + (1-r_x)(1-a_x)r_y(1-L_1)^2L_2 +$$
$$(1-r_x)(1-a_x)(1-r_y)a_y(1-t_y)v_z(1-L_1)L_2 +$$
$$(1-r_x)(1-a_x)(1-r_y)(1-a_y)r_z(1-L_1)L_2]$$

$$Pr(0011 \mid M) = [(1-L_1)^2L_1L_2r_x + (1-r_x)a_x(1-t_x)v_y(1-L_1)L_1L_2 +$$
$$(1-r_x)a_x(1-t_x)(1-v_y)(1-t_y)v_zL_1L_2 +$$
$$(1-r_x)a_x(1-t_x)(1-v_y)(1-t_y)(1-v_z)t_zb_zL_2 +$$
$$(1-r_x(1-a_x)r_y(1-L_1)L_1L_2 + (1-r_x)(1-a_x)(1-r_y)$$
$$a_y(1-t_y)v_zL_1L_2 + (1-r_x)(1-a_x)(1-r_y)a_y(1-t_y)$$
$$(1-v_z)t_zb_zL_2 + (1-r_x)(1-a_x)(1-r_y)(1-a_y)r_zL_1L_2 +$$
$$(1-r_x)(1-a_x)(1-a_y)(1-r_z)a_zt_zb_zL_2]$$

$$Pr(0101 \mid M) = [(1-L_1)^2L_1L_2r_x + (1-r_x)a_x(1-t_x)v_yL_1(1-L_1)L_2 +$$
$$(1-r_x)a_x(1-t_x)(1-v_y)t_yb_y(1-L_1)L_2 +$$
$$(1-r_x)a_x(1-t_x)(1-v_y)y(1-b_y)v_z(1-b_y)v_z(1-L_1)L_2 +$$
$$(1-r_x)(1-a_x)r_yL_1(1-L_1)L_2 +$$
$$(1-r_x)(1-a_x)(1-r_y)a_yt_yb_y(1-L_1)L_2 +$$
$$(1-r_x)(1-a_x)(1-r_y)a_yt_y(1-b_y)v_z(1-L_1)L_2]$$

$$Pr(0111 \mid M) = [(1-L_1)L_1^2L_2r_x + (1-r_x)a_x(1-t_x)v_yL_1^2L_2 +$$
$$(1-r_x)a_x(1-t_x)(1-v_y)t_yb_yL_1L_2 +$$
$$(1-r_x)a_x(1-t_x)(1-v_y)t_y(1-b_y)v_zL_1L_2 +$$
$$(1-r_x)a_x(1-t_x)(1-v_y)t_y(1-b_y)(1-v_z)t_zb_zL_2 +$$
$$(1-r_x)(1-a_x)r_yL_1^2L_2 + (1-r_x)(1-a_x)(1-r_y)a_yt_yb_y$$
$$L_1L_2 + (1-r_x)(1-a_x)(1-r_y)a_yt_y(1-b_y)v_2L_1L_2 +$$
$$(1-r_x)(1-a_x)(1-r_y)a_yt_y(1-b_y)(1-v_z)t_zb_zL_2]$$

$$Pr(1000 \mid M) = [L_1(1-L_1)^2(1-L_2)r_x + (1-r_x)a_xt_xb_x(1-L_1)^2(1-L_2) +$$
$$(1-r_x)a_xt_x(1-b_x)v_y(1-L_1)^2(1-L_2) +$$
$$(1-r_x)a_xt_x(1-b_x)(1-v_y)(1-t_y)v_z(1-L_1)(1-L_2) +$$
$$(1-r_x)a_xt_x(1-b_x)(1-v_y)(1-t_y)(1-v_z)(1-t_z)]$$

-continued $$Pr(1100 \mid M) = [L_1^2(1-L_1)(1-L_2)r_x + (1-r_x)a_xt_xb_xL_1(1-L_1)(1-L_2) +$$
$$(1-r_x)a_xt_x(1-b_x)v_yL_1(1-L_1)(1-L_2) + (1-r_x)$$
$$a_xt_x(1-b_x)(1-v_y)t_yb_y(1-L_1)(1-L_2) + (1-r_x)$$
$$a_xt_x(1-b_x)(1-v_y)t_y(1-b_y)v_z(1-L_1)(1-L_2) +$$
$$(1-r_x)a_xt_x(1-b_x)(1-v_y)t_y(1-b_y)(1-v_z)(1-t_z)]$$

$$Pr(1010 \mid M) = [L_1^2(1-L_1)(1-L_2)r_x + (1-r_x)a_xt_xb_xL_1(1-L_1)L_1(1-L_2) +$$
$$(1-r_x)a_xt_x(1-b_x)v_yL_1(1-L_1)L_1(1-L_2) + (1-r_x)$$
$$a_xt_x(1-b_x)(1-v_y)(1-t_y)v_xL_1(1-L_2) + (1-r_x)$$
$$a_xt_x(1-b_x)(1-v_y)(1-t_y)(1-v_z)t_zb_z(1-L_2) +$$
$$1(r_x)a_xt_x(1-b_x)(1-v_y)(1-t_y)(1-v_z)t_z(1-b_z)]$$

$$Pr(1110 \mid M) = [L_1^3(1-L_2)r_x + (1-r_x)a_xt_xb_xL_1^2(1-L_2) +$$
$$(1-r_x)a_xt_x(1-b_x)v_yL_1^2(1-L_2) +$$
$$(1-r_x)a_xt_x(1-b_x)(1-v_y)t_yb_yL_1(1-L_2) +$$
$$(1-r_x)a_xt_x(1-b_x)(1-v_y)t_y(1-b_y)v_z$$
$$L_1(1-L_2) + (1-r_x)a_xt_x(1-b_x)a_xt_x(1-b_x)$$
$$(1-v_y)t_y(1-b_y)(1-v_z)t_zb_z(1-L_2) + (1-r_x)$$
$$a_xt_x(1-b_x)(1-v_y)t_y(1-b_y)(1-v_z)t_z(1-b_z)]$$

$$Pr(1001 \mid M) = [L_1(1-L_1)^2L_2r_x + (1-r_x)a_xt_xb_x(1-L_1)^2L_2 + (1-r_x)$$
$$a_xt_x(1-b_x)v_y(1-L_1)^2L_2 + (1-r_x)a_x$$
$$t_x(1-b_x)(1-v_y)(1-t_y)v_z(1-L_1)L_2]$$

$$Pr(1101 \mid M) = [L_1^2(1-L_1)L_2r_x + (1-r_x)a_xt_xb_xL_1(1-L_1)L_2 +$$
$$(1-r_x)a_xt_x(1-b_x)v_yL_1(1-L_1)L_2 + (1-r_x)$$
$$a_xt_x(1-b_x)(1-v_y)t_yb_y(1-L_1)L_2 + (1-r_x)$$
$$a_xt_x(1-b_x)(1-v_y)t_y(1-b_y)v_z(1-L_1)L_2]$$

$$Pr(1011 \mid M) = [L_1^2(1-L_1)l_2r_x + (1-r_x)a_xt_xb_x(1-L_1)L_1L_2 +$$
$$(1-r_x)a_xt_x(1-b_x)v_y(1-L_1)L_1L_2 + (1-r_x)$$
$$a_xt_x(1-b_x)(1-v_y)(1-t_y)v_zL_1L_2 + (1-r_x)$$
$$a_xt_x(1-b_x(1-v_y)(1-t_y)(1-v_z)t_zb_zL_2]$$

$$Pr(1111 \mid M) = [L_1^3L_2r_x + (1-r_x)a_xt_xb_xL_1^2L_2 + (1-r_x)a_xt_x(1-b_x)v_yL_1^2$$
$$L_2 + (1-r_x)a_xt_x(1-b_x)(1-v_y)t_yb_yL_1L_2 +$$
$$(1-r_x)a_xt_x(1-b_x)(1-v_y)t_y(1-b_y)v_zL_1L_2 +$$
$$(1-r_x)a_xt_x(1-b_x)(1-v_y)$$
$$t_y(1-b_y)(1-v_z)t_zb_zL_2]$$

Figure 5B:
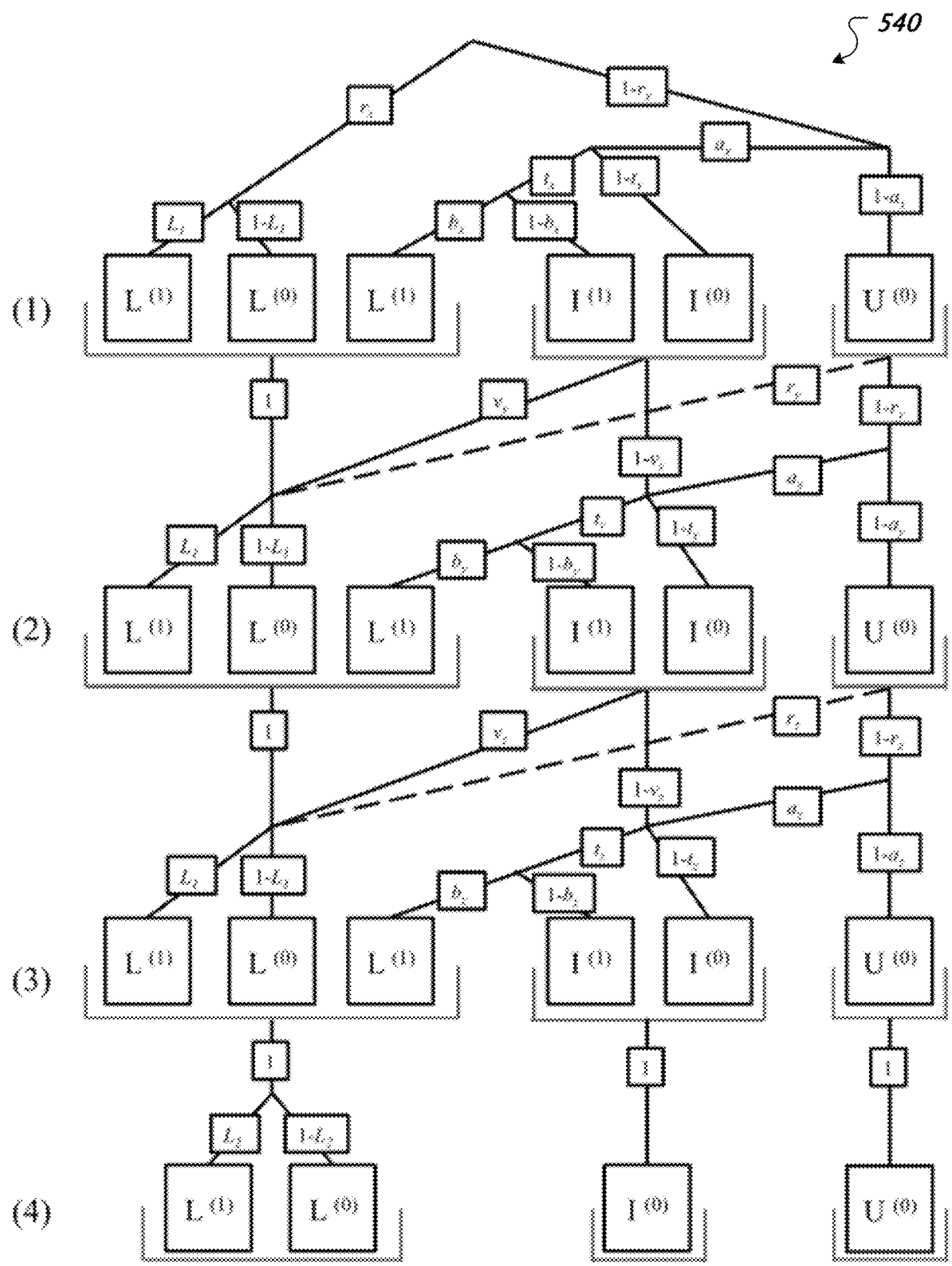
FIG. 5B shows a tree diagram of how the probabilities of each of 16 response patterns of any given item can be determined according to an example of an implementation.

The above formulae can be used to compute probabilities of the 16 response patterns, given any item, the allowable cognitive state sequences, and the Hidden Markov Model of an n-item, free recall task with three study-test trials and one delayed test trial FIG. 5B shows a tree diagram 540 of how the probabilities of each of 16 response patterns of any given item can be determined according to an example of an implementation. The tree diagram 540 represents the HMM being used to compute item response pattern probabilities given in the 16 formulae above. Superscripts $^{(0)}$ and $^{(1)}$ indicate the response made by the subject. Boxes containing the superscripts specify the state in the state sequence.

ADAS-Cog Example: computing item response pattern probability for {0000}. For any given item's response pattern, such as 0000, its probability can be computed as follows. Step 1: specify the possible cognitive state sequences, from UUUU to LLLL, that are allowable for the given response pattern (see e.g., Table 2 in FIG. 5D). Step 2: compute the probability of occurrence of each of these possible cognitive state sequences, given the response pattern (e.g., 0000). Step 3: add together the probabilities of the possible cognitive state sequences for the given response pattern to determine the probability of the response pattern, given the model.

In addition, Bayesian inference methods can be used to estimate the HMM's parameters from observed data with j response categories and k items. The response patterns are the probability of occurrence of each response pattern (e.g., 0010, see the 16 formulae above) given the item's list position. Since the response pattern probabilities sum to 1, and range in [0,1], the likelihood function of the model is a multinomial distribution. To analyze individual subject observed data, Bayesian inference methods can be used to estimate each of the model's seven parameter values. Each parameter estimate for an individual is drawn from a Gaussian distribution, with means, μ, and standard deviations, σ, corresponding to group level parameters. For each model parameter, the initial Gaussian distribution parameters can be set as follows: the initial value of μ is a random value from a normal distribution, and the initial value of σ is randomly drawn from a Gamma distribution.

Using Bayesian inference techniques for the hierarchical model, the probability distributions for each parameter can be obtained from a logit inverse of the population Gaussian distribution, specified in the following way:

$$v_{k,i} \sim \text{Logit}^{-1}[\text{Gaussian}(\mu_k^v, \sigma_k^v)]$$

$$t_{k,i} \sim \text{Logit}^{-1}[\text{Gaussian}(\mu_k^t, \sigma_k^t)]$$

$$a_{k,i} \sim \text{Logit}^{-1}[\text{Gaussian}(\mu_k^a, \sigma_k^a)]$$

$$b_{k,i} \sim \text{Logit}^{-1}[\text{Gaussian}(\mu_k^b, \sigma_k^b)]$$

$$r_{k,i} \sim \text{Logit}^{-1}[\text{Gaussian}(\mu_k^r, \sigma_k^r)]$$

$$L_{k,i} \sim \text{Logit}^{-1}[\text{Gaussian}(\mu^{L1}, \sigma^{L1})]$$

Estimates for each of 52 parameters can be taken from Gaussian probability distributions with unknown hyper-parameters, μ and σ. An inverse-logit can be applied to the estimate provided by the Gaussian distribution to take the estimates from all Reals down to [0,1] space. Evidence provided by the group can be used to refine the estimates for the hyper-parameters, belonging to each parameter, from their hyper-distribution. To keep the order constraints on r and t, an appropriate order constraint can be imposed on their hyper-parameters and on the model parameter values.

The model described in FIG. 5b is for any n-item recall task with three study-test trials and one delayed test trial. The model may be extended to any number of test or study-test trials by adding additional a, b, r, t, and v parameters as dictated by whether the trial is a study or study-test trial. Also, a new subscript is added to these parameters for each added trial. The model may also be extended to any number of delayed test trials by adding additional retrieval parameters, $L_{t,i}$, from Learned State, L, to account for further decay in either storage or retrieval strength from L, over the time course of the delayed test trials. Parameters are estimated for each response pattern and each item. Thus, each parameter of the Hierarchical Hidden Markov Model can be estimated using Bayesian inference techniques.

Once the initial Gaussian distribution parameters, μ and σ, are selected from the appropriate prior distribution for each HMM group level parameter, Bayesian sampling methods can be used to constrain each model parameter's range to [0,1]. The inverse logit is applied to the values drawn from the model parameter's group-level Gaussian distribution. The Gaussian distribution parameters, μ and σ, are hyperparameters whose values are refined by data from the group (e.g., mild cognitive impairment), to which the individual whose parameters are being estimated, belongs.

Measuring Individual Subject Performance: ADAS-Cog HMM. HMMs have been predominantly used to focus on the cognitive processes that take place in a group of healthy subjects to allow generalization of results to the population. Similar to these models, models in accordance with the systems and techniques described herein can estimate group-level cognitive parameters. However, the present models differ from prior models in that they can also estimate cognitive processes at the individual level for cognitively impaired and cognitively normal subjects. The models can also account for the effect of the position in which each item of a memory task is presented in each study trial. These extensions to the HMM can facilitate such group- and individual-level estimations.

Figure 5C:
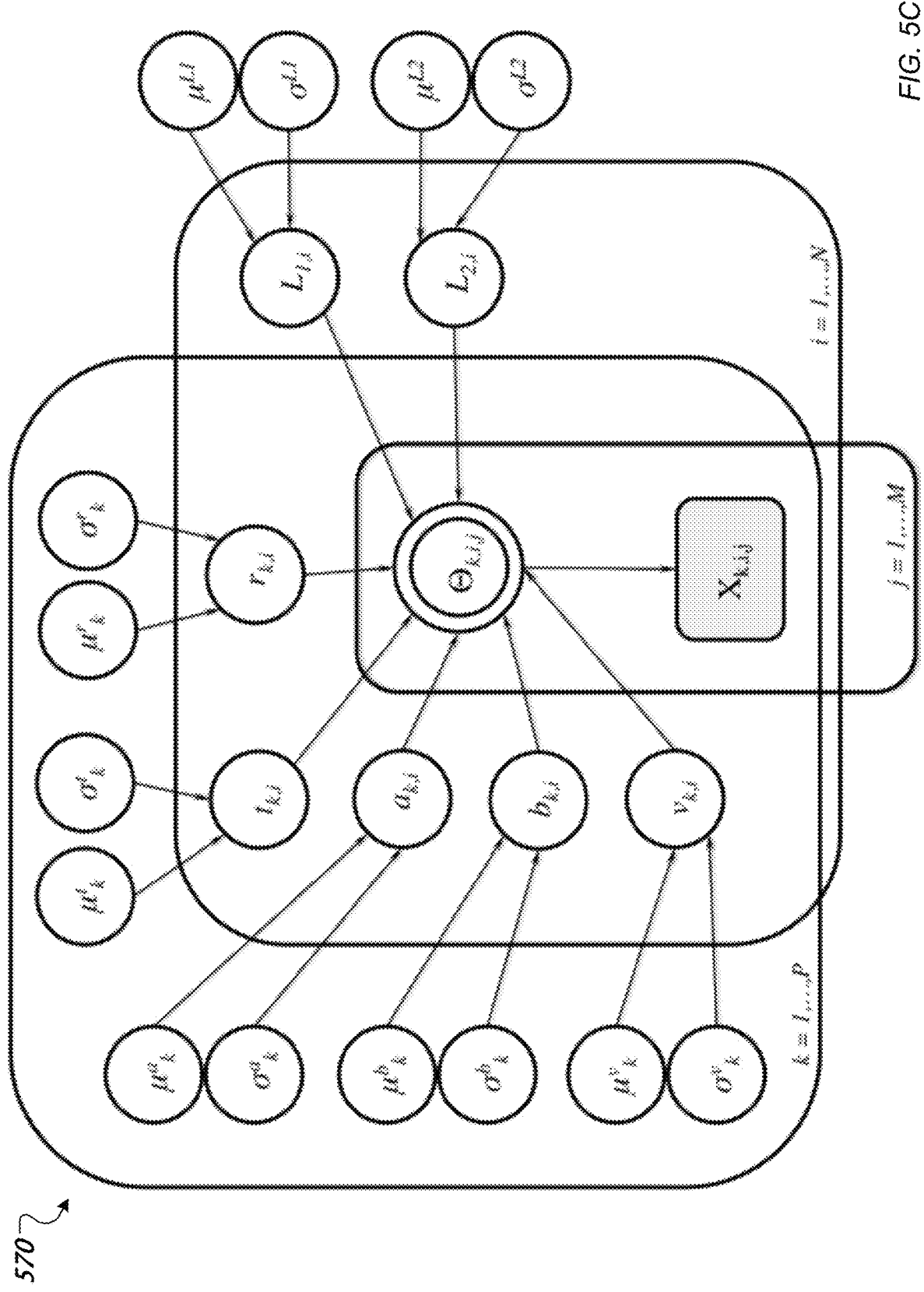
FIG. 5C shows an expansion of the HMM into a hierarchical structure, which permits estimation of cognitive processing parameters at the individual subject level, within the subject's group, for the item's list position, and for the item's response pattern.

FIG. 5C shows an expansion of the HMM into a hierarchical structure, which permits estimation of cognitive processing parameters at the individual subject level, i (i= 1 . . . , N) within the subject's group for the item's list position, k, (k=1 . . . , P), and for the item's response pattern (j 1, . . . , M). The ADAS-Cog instantiation of the model has 52 parameters at the group-by-item level –1 for each of the 10 list positions, k, for the r, a, v, b and t cognitive parameters, plus 1 for the $L_1$ and 1 for the $L_2$ cognitive parameters. At the group level, all individuals in that group share the same parameter estimates for each of the model's 52 cognitive parameters, the initial values of which are specified by a uniform prior distribution. At the individual subject level, 52 parameters unique to that subject can be estimated. The total number of model parameters will therefore be 52×N, where N is the number of subjects.

A graphical Hierarchical Markov Model 570 also shows how to predict individual subject performance on each of the 16 response patterns for any given list item. $X_{k,i,j}$ represents the observed data input for the model, where X is the 4-tuple response pattern of a given item over four trials (e.g., 0010); k=1, . . . , P, where k is the item's list position; i=1, . . . , N, where i is the individual; and j=1, . . . , M, where j is the item's response pattern. $\Theta_{k,i,j}$ represents the predicted response, expressed as the probability of a given item list position, k, given the item response pattern, j, and the individual subject, i, given the model. The remaining nodes are the model's parameters. Note that the nodes directly connected to $\Theta_{k,i,j}$ are the model parameters of interest and the remaining nodes, are hyper-parameters, which are the means and variances of each parameter's hierarchical Gaussian distribution. See "Lee, M. D. & Wagenmakers, E. J. Bayesian modeling for cognitive science: A practical course. 2014. *Cambridge University Press*", which is hereby incorporated by reference, for details.

Estimation of the individual level parameters is possible using the hierarchical model shown in FIG. 5C, which assumes that an individual's parameter estimates are drawn from a hierarchical distribution with unknown hyper-parameters defining the individual's group. See the Bayesian inference techniques described above for the hierarchical parameter distributions.

Using data gathered from cognitively normal subjects, standard memory theory suggests that items located at the beginning of the list have a higher probability of entering into short-term memory (the L state) while the items towards the end of the list are more likely to be recalled from working memory (the I state). The model's r parameter is the transition probability of storage into short-term memory from the unlearned state, so the pattern produced by the P "r" parameters for the P list positions should reflect the primacy effect described by memory theory.

Figure 6:
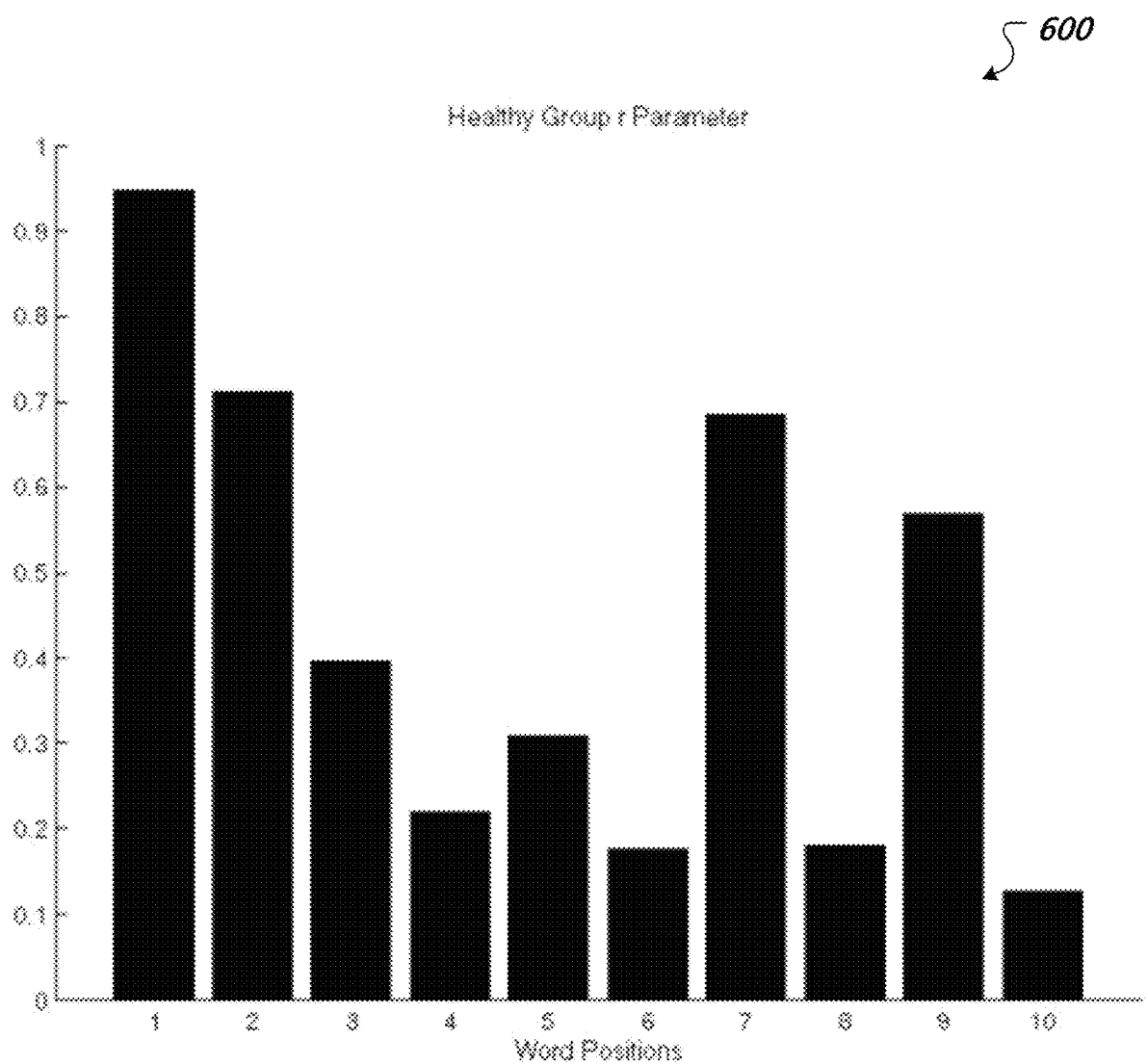
FIG. 6 shows a graph of the probability of transitioning from an Unlearned state to the Learned stated during ADAS-Cog study-test trials.

FIG. 6 shows a graph 600 of the probability of transitioning from an Unlearned state, U, to the Learned stated, L (short-term memory), during ADAS-Cog study-test trials (the r parameter). FIG. 6 shows the means of the posterior distributions in the Bayesian analysis for the 10 "r" parameters corresponding to the 10 word positions in the study list for cognitively normal subjects tested with the ADAS-Cog wordlist memory task. The r parameters belonging to the first three list positions are the highest. The only exceptions to the list position (a.k.a. serial position) effect are for word positions 7 and 9, which are increased for reasons, idiosyncratic to the ADAS-Cog wordlist memory task (e.g. increased associability of words 7 and 9 with other list words).

Figure 7:
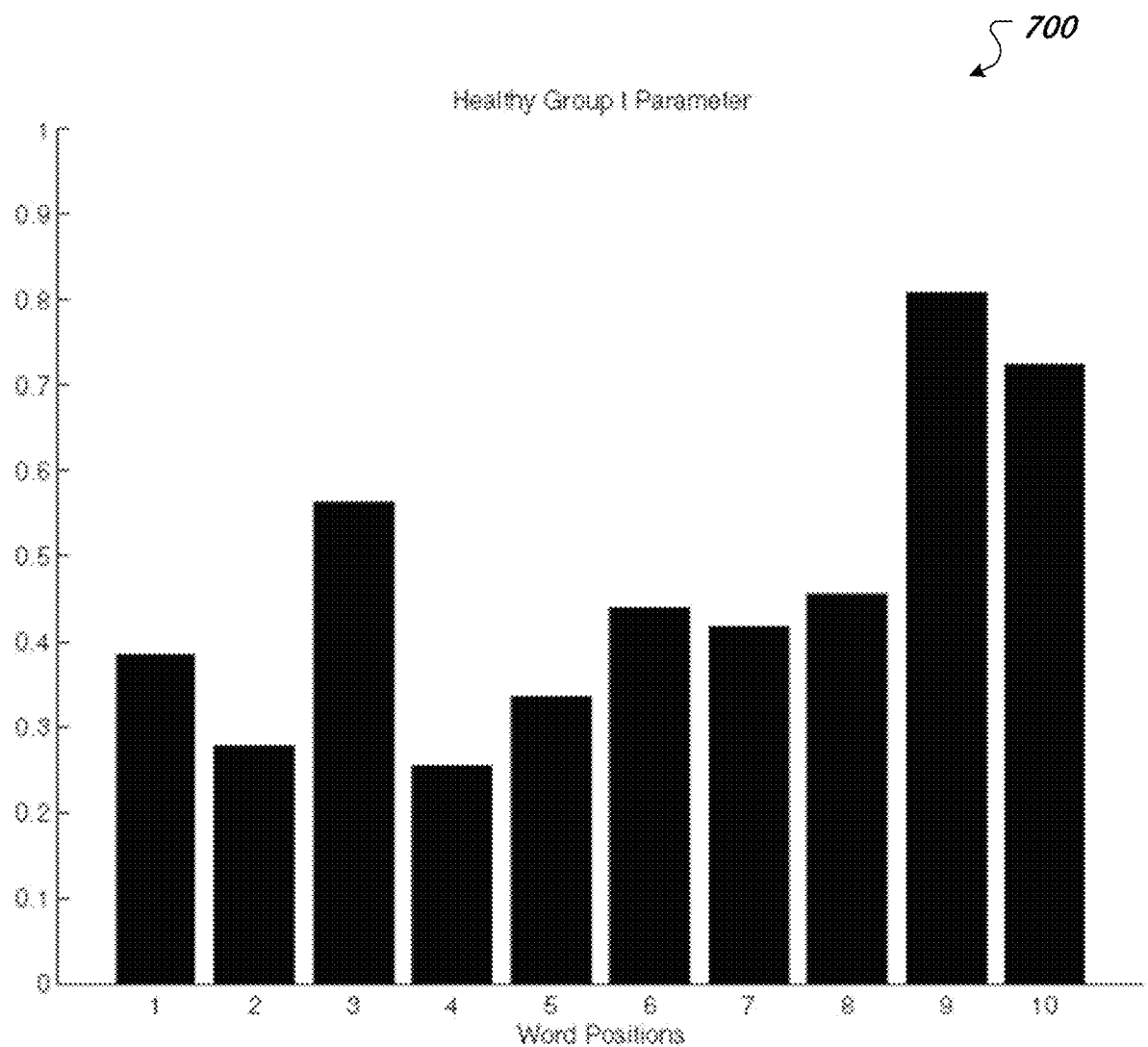
FIG. 7 shows a graph of the serial position effects of a parameter modelling retrieval of items from working memory during ADAS-Cog study-test trials.

FIG. 7 shows a graph 700 of the probability of recalling a word from working memory (the Intermediate state, I) during ADAS-Cog study-test trials (the t parameter). FIG. 7 shows the serial position effects of the t parameter, which retrieves items from working memory (the I state). The t parameter values gradually increase as list position approaches the list's end. The only exception to this serial position effect is word position 3, which is increased for reasons idiosyncratic to the ADAS-Cog wordlist memory task.

Figure 8:
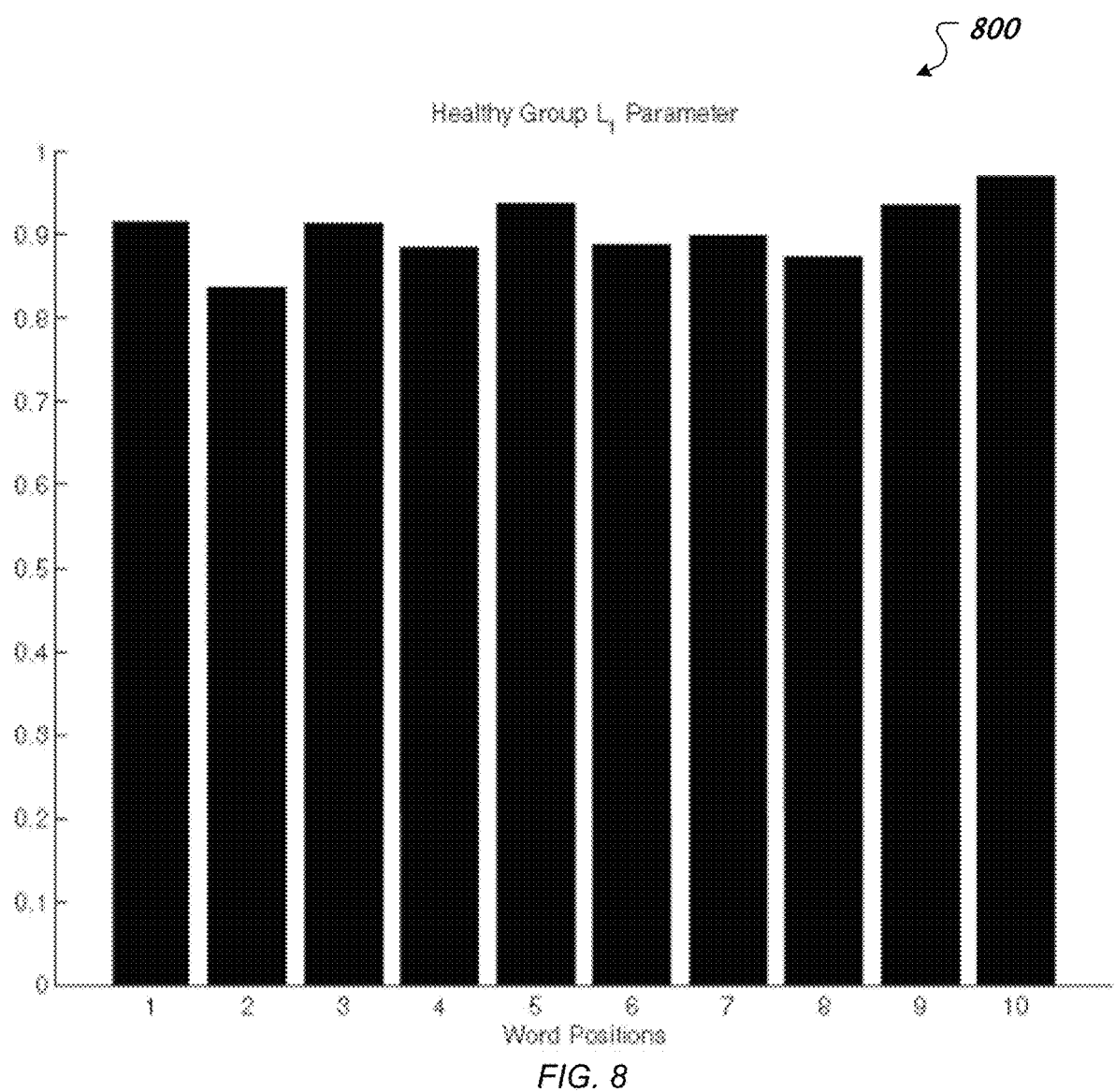
FIG. 8 shows a graph of the serial position effects of a parameter modelling retrieval of items from short-term memory during ADAS-Cog study-test trials.

FIG. 8 shows a graph 800 the probability of recalling a word from short-term memory (state L) during ADAS-Cog study-test trials (the $L_1$ parameter). FIG. 8 shows the serial position effects of the $L_1$ parameter, which retrieves items from short-term memory during the ADAS-Cog study-test trials. The $L_1$ parameter does not significantly vary across list positions for cognitively normal subjects. This suggests that, for ADAS-Cog study-test trials retrieving from short-term memory (state L), a single cognitive process retrieves list items regardless of their order of presentation during the study trials.

The identified exceptions in the behavior of the cognitive processing parameters, which are idiosyncratic to the ADAS-Cog wordlist memory task, inject noise into the parameter estimates. This noise can be reduced by adding order constraints to the r and t parameters, and by reducing the dimensionality of $L_1$ and $L_2$. The order constraints on both the r and t parameters are: if j<k then $r_j > r_k$ and $t < t_k$. Imposing these order constraints on r and t does not reduce the number of parameters, but changes their relationships to each other. In contrast, the numbers of $L_1$ and $L_2$ parameters are both reduced from 10 to 1, due to the lack of a position effect on their recall probabilities. This means that short-term memory is invariant to item study list position.

The detailed examples above have focused on implementations using the ADAS-Cog test. Now the serial position effects will be evaluated with reference to implementations that use the AVLT test.

Figure 9A:
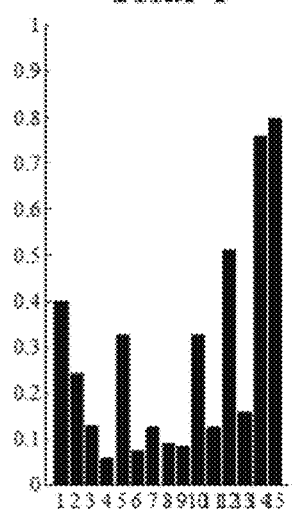
FIGS. 9A-9N show the serial position curves for the seven trials of the AVLT recall task for normal aging (healthy) and AD subjects.
Figure 9B:
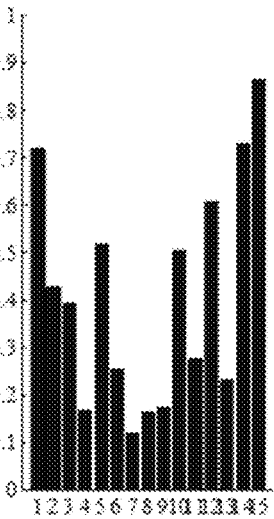
Figure 9C:
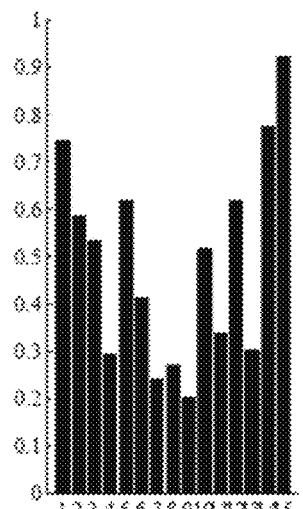
Figure 9D:
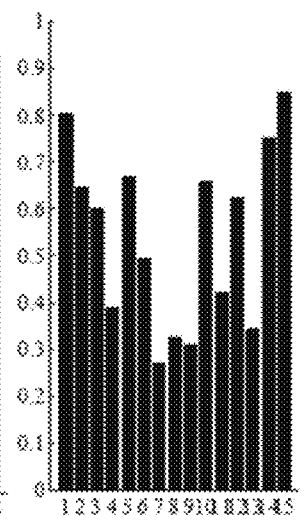
Figure 9E:
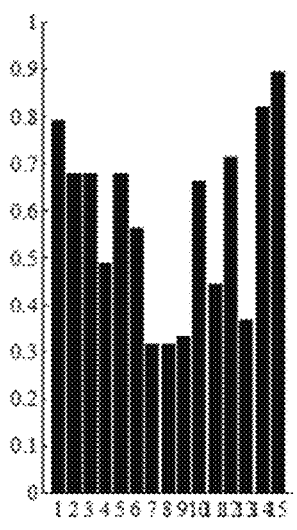
Figure 9F:
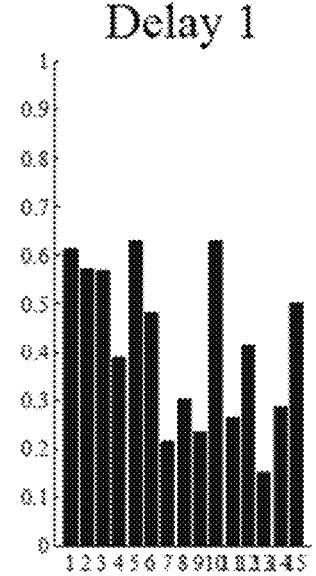
Figure 9G:
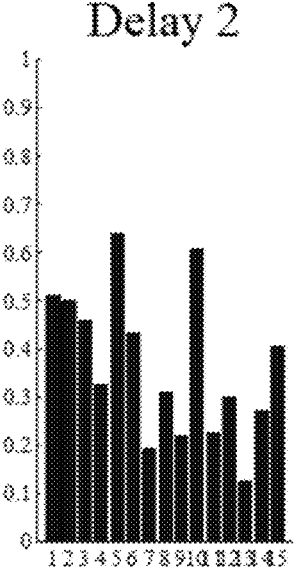
Figure 9H:
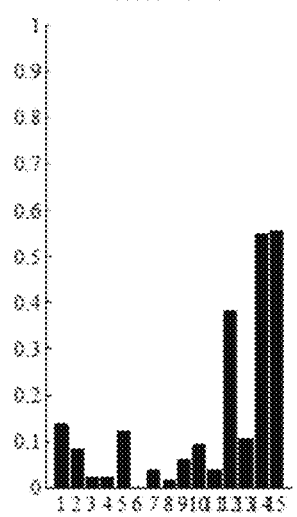
Figure 9I:
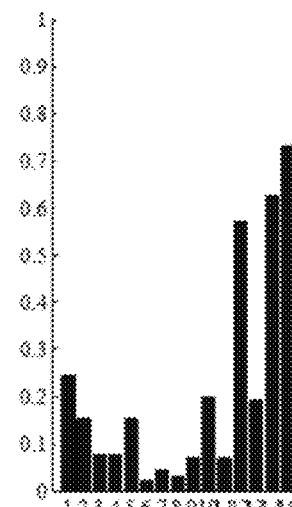
Figure 9J:
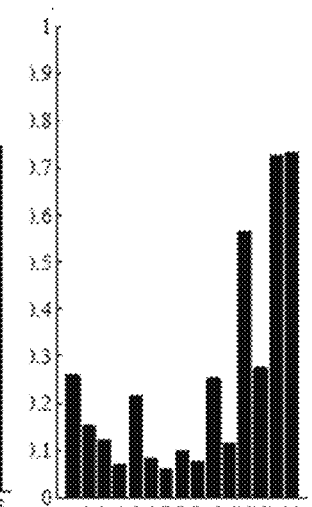
Figure 9K:
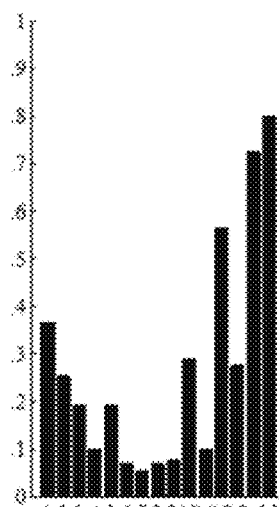
Figure 9L:
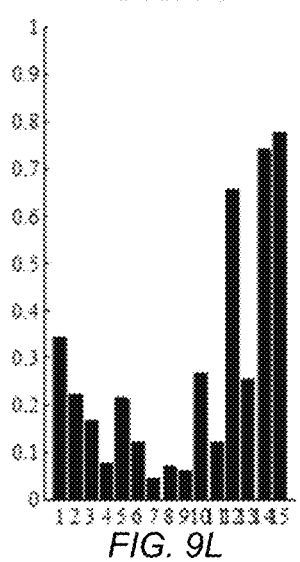
Figure 9M:
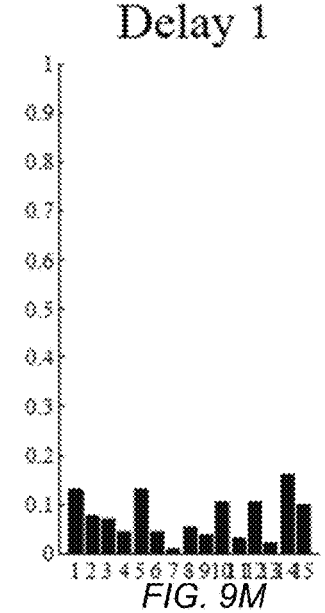
Figure 9N:
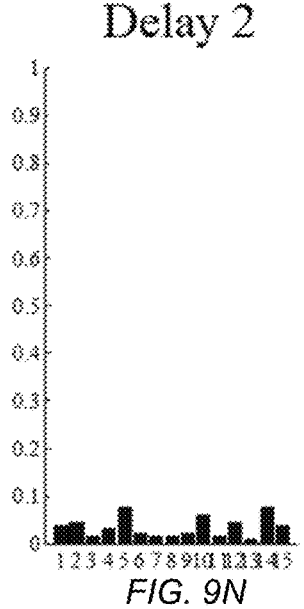

FIGS. 9A-9N show the serial position curves for the seven trials of the AVLT recall task for normal aging (Healthy) and AD subjects. FIG. 9A shows the probability of recall against serial position for trial 1 with healthy subjects. FIG. 9B shows the probability of recall against serial position for trial 2 with healthy subjects. FIG. 9C shows the probability of recall against serial position for trial 3 with healthy subjects. FIG. 9D shows the probability of recall against serial position for trial 4 with healthy subjects. FIG. 9E shows the probability of recall against serial position for trial 5 with healthy subjects. FIG. 9F shows the probability of recall against serial position for delay 1 with healthy subjects. FIG. 9G shows the probability of recall against serial position for delay 2 with healthy subjects.

FIG. 9H shows the probability of recall against serial position for trial 1 with AD subjects. FIG. 9I shows the probability of recall against serial position for trial 2 with AD subjects. FIG. 9J shows the probability of recall against serial position for trial 3 with AD subjects. FIG. 9K shows the probability of recall against serial position for trial 4 with AD subjects. FIG. 9L shows the probability of recall against serial position for trial 5 with AD subjects. FIG. 9M shows the probability of recall against serial position for delay 1 with AD subjects. FIG. 9N shows the probability of recall against serial position for delay 2 with AD subjects.

In general, the first (primacy) and last (recency) items are more likely to be recalled than items in the middle of the list. There are some exceptions, such as items 5 and 10, which have inordinately high recall probabilities on study-test trial 1 relative to their serial position. This violation of serial position effect may be due to associability with other items. As the number of study-test trials increases, the primacy and recency positions peak in their recall probabilities earlier than items in other list positions. Both normal aging and AD group shows this pattern, with the AD group showing lower recall probabilities for all list positions, but showing less of a reduction for items 11 to 15, which occupy recency positions. For the delayed test trials, the AD group shows uniformly reduced recall probabilities compared to the normal aging group.

Although these observations of the pattern of recall probabilities as a function of serial position, trial number and delay are useful, they do not provide useful interpretation of the cognitive processes underlying memory task performance in normal aging and AD. To understand if there are cognitive processes selectively affected by AD may require what are called, "generative models", which specify a set of cognitive processes that predict recall task performance from the item response data of memory tests.

The AVLT recall task data are described above. In addition, an AVLT instantiation of the HMM can be the same as that of the ADAS-Cog HMM, except for the following modifications: (1) There are 21 allowable memory state sequences of U, I and L for the 7 trials of the AVLT recall task (see Table 3 in FIG. 5E); (2) There are 128 item response patterns for which one must compute the probabilities of each response pattern, from {0000000 to 1111111}, given a particular list item, the allowable cognitive state sequences for that response pattern, and the AVLT instantiation of the HMM (see the Appendix); (3) There are two additional parameters in state, L ($l_{31}$ and $l_{32}$), which allow its strength of storage to be weaker than those of parameters, $l_1$ and $l_2$. These parameters were added to model the recall performance at the one hour delayed test trial ($l_{32}$) and to allow for the possibility of a 2nd, weaker strength of storage for items recalled from state L during AVLT study-test trials ($l_{31}$) (see the Appendix); and (4) The trial-dependent parameter values are no longer 1 because some of the cognitive process parameter distributions are not stationary after study-test trial 1 (see the Trial-Dependent Parameters Code Example below).

Table 3 in FIG. 5E is the Seven Trial Cognitive States Table, which shows the possible cognitive state sequences for a given pattern of responses for a given list item in a seven trial recall task with five study-test trials and two delayed test trials (such as in the AVLT).

The possible cognitive state sequences for a given pattern of responses for a given list item in a seven trial recall task with five study-test trials and two delayed test trial. The Hidden Markov Model consists of three latent cognitive states. U: Unlearned state. I: Intermediate state. L: Learned state. The cognitive state in each column indicates the state the item is in at the conclusion of that trial. Note that not all cognitive state sequences are possible for any given pattern of item responses.

During the study-test trials, if a given item is correctly recalled from state, I, during the test part of the study-test trial, it can transfer it into the learned state, L, via cognitive process, b. Note that if, on the previous trial, the item was in state, U, it can still transfer into state, L, via cognitive process, b, during the test part of the current study-test trial, because the item could have transferred from state U, to I, during the study part of the current study-test trial. A given item can also transfer into state, L, during the study part of the study-test trial, via cognitive process, r, if the item was in state, U, on the previous trial, or via cognitive process, v, if the item was in state, I, on the previous trial. The cognitive state sequences that have two ways of being transferred into state, L, have state, L, and the previous state, U or I, highlighted with bold text and double borders.

In addition, trial-dependent parameter can be used to achieve stationary cognitive process parameter distributions. The following is a Trial-Dependent Parameters Code Example to achieve stationary cognitive process parameter distributions in an AVLT HMM instantiation:

Note: Beta(1,1)=Uniform(0,1)
Definitions
f=AVLT recall trial number
k=AVLT list item number
The cognitive process parameter, v, reaches a stationary distribution by f=trial 3.

```
for (f in 3:4) {
  for (k in 1:N) {
    v[f,k] <- v1[k]
  }
}
```

Reduce Cognitive Process Parameter, v, by Trial-Dependent parameter, v2[f], for trials, f=1, 2.

```
for (f in 1:2) {
  for (k in 1:N) {
    v[f,k] <- v1[k]*v2[f]
  }
}
```

Set Prior Probabilities for Trial-Dependent Parameters, v2[f], of Cognitive Process, v to a beta distribution.

```
for (f in 1:2) {
  v2[f] ~ dbeta(1,1)
}
```

The cognitive process parameters, r, t, L1, a, and b, reach a stationary distribution by f=trial 3.

```
for (f in 4:5) {
  for (k in 1:N) {
    r[f,k] <- r1[k]
    t[f,k] <- t1[k]
    L1[f,k] <- L11[k]
    a[f,k] <- a1[k]
    b[f,k] <- b1[k]
  }
}
```

Reduce cognitive process parameters, r, t, L1, a, and b, by Trial-Dependent parameters,

```
r2[f], t2[f], L12[f], a2[f], and b2[f] for trials, f = 1, 2, 3.
for (f in 1:3) {
  for (k in 1:N) {
    r[f,k] <- r1[k]*r2[f]
    t[f,k] <- t1[k]*t2[f]
    L1[f,k] <- L11[k]*L12[f]
    a[f,k] <- a1[k]*a2[f]
    b[f,k] <- b1[k]*b2[f]
  }
}
```

Set Prior Probabilities for Trial-Dependent Parameters, r2[f], t2[f], L12[f], a2[f], and b2[f], of cognitive process parameters, r, t, L1, a, and b, to a beta distribution.

```
for (f in 1:3) {
  r2[f] ~ dbeta(1,1)
  t2[f] ~ dbeta(1,1)
  a2[f] ~ dbeta(1,1)
  b2[f] ~ dbeta(1,1)
  L12[f] ~ dbeta(1,1)
}
```

Set Prior Probabilities for List Item 1, of Cognitive Process Parameters, r and t, to a beta distribution. Organize the t parameter to be increasing.

```
t1 <- sort(tt1)
r1[1] ~ dbeta(1,1)
tt1[1] ~ dbeta(1,1)
```

Organize the Cognitive Process Parameters, r and t, for list items 2-15 to be decreasing by multiplying the previous r1 and tt1 with a prior distribution specified by rr and tt.

```
for (k in 2:15) {
  r1[k] <- r1[k-1] * rr[16-k]
  tt1[k] <- tt1[k-1] * tt[16-k]
}
```

Assign a Beta Distribution to the Prior Probabilities of the Parameters, rr and tt, for List Items, 2 to 15.

```
rr <- sort(rht)
tt <- sort(tht)
for (k in 1:14) {
  rht[k] ~ dbeta(1,1)
  tht[k] ~ dbeta(1,1)
}
```

Set Prior Probabilities of the Cognitive Process Parameters, a, b, v, L1, L2, L31, and L32 to a beta distribution for all List Items, 1 to N.

```
for (k in 1:N) {
  a1[k] ~ dbeta(1,1)
  b1[k] ~ dbeta(1,1)
  v1[k] ~ dbeta(1,1)
  L11[k] <- LL1
  L2[k] <- LL2
  L31[k] <- LL31
  L32[k] <-LL32
}
LL1 ~ dbeta(1,1)
LL2 ~ dbeta(1,1)
LL31 ~ dbeta(1,1)
LL32 ~ dbeta(1,1)
}
```

Calculating the Probability of a Given Item Response Pattern: The calculation can be done in the same manner as presented above with respect to Table 1, except it is done over the 7 trials of the AVLT recall task data, and there are 5 subscripts instead of 3, which represent the AVLT's 5 study-test trials. Also, Table 1 does not show the trial-dependent parameters because all cognitive process parameters had a stationary distribution by the end of the study-trial one. In the AVLT instantiation of the HMM, the trial-dependent parameters are included in each cell's calculation of a given study-test trial and response pattern until the cognitive process parameter has a stationary distribution, which is indicated by the trial-dependent parameter reaching a value that does not change over successive trials.

Achieving Stationary Distributions of AVLT Cognitive Process Parameters: Each cognitive process requires a number of study or study-test trials for its parameter to reach a distribution that does not change over subsequent trials or time (stationary). For the ADAS-Cog recall task, all cognitive process parameters had a stationary distribution by the end of study-test trial 1. However, as will be discussed next, this stationarity did not occur after study-test trial 1 for some of the cognitive process parameters of the AVLT recall task data.

Figure 10A:
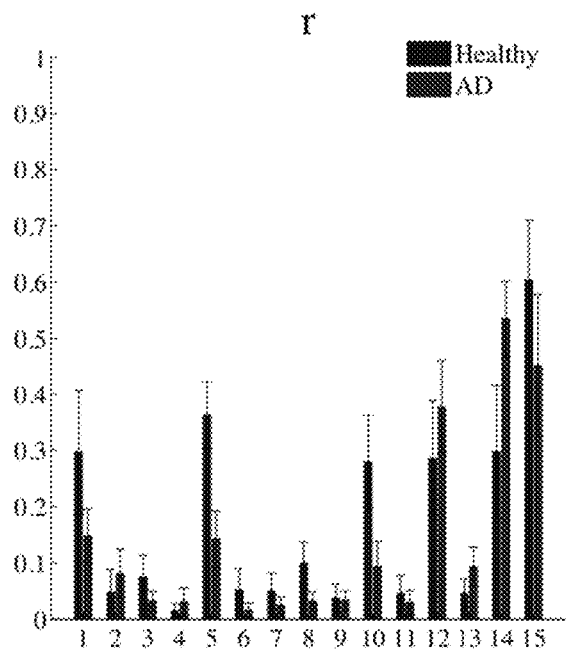
FIGS. 10A-10H show cognitive process parameter probabilities using the AVLT recall task data applied to an HMM developed for the ADAS-Cog recall task.
Figure 10B:
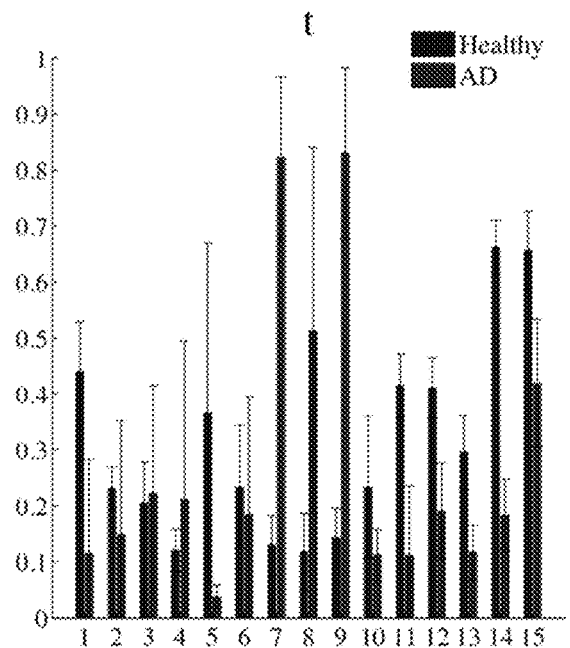
Figure 10C:
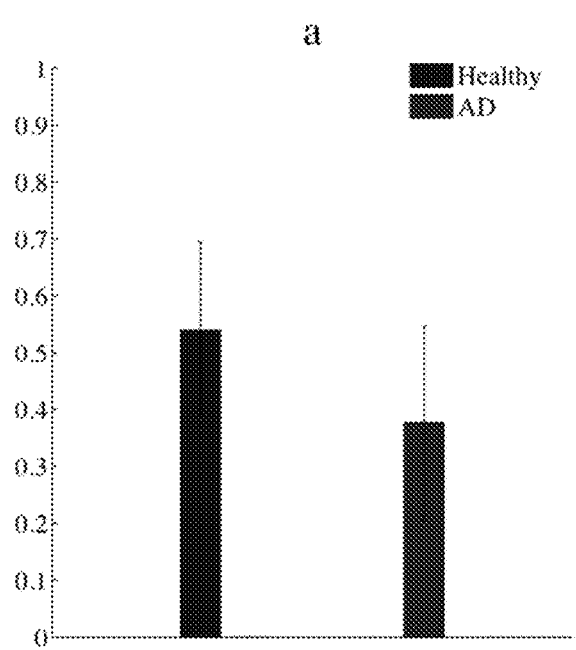
Figure 10D:
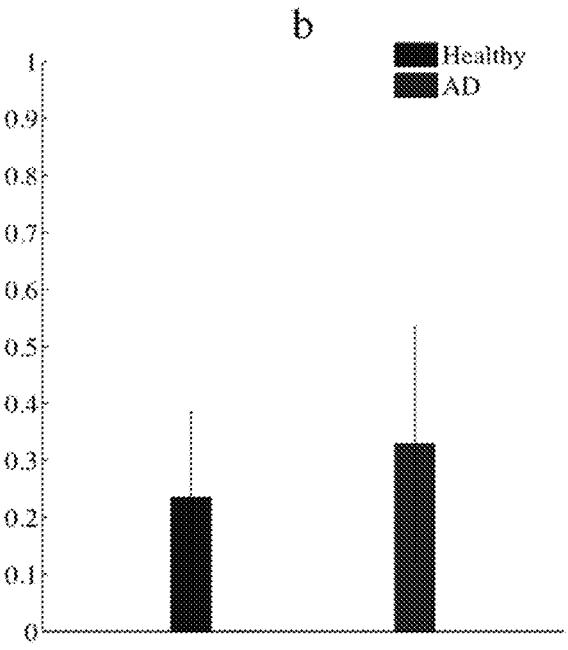
Figure 10E:
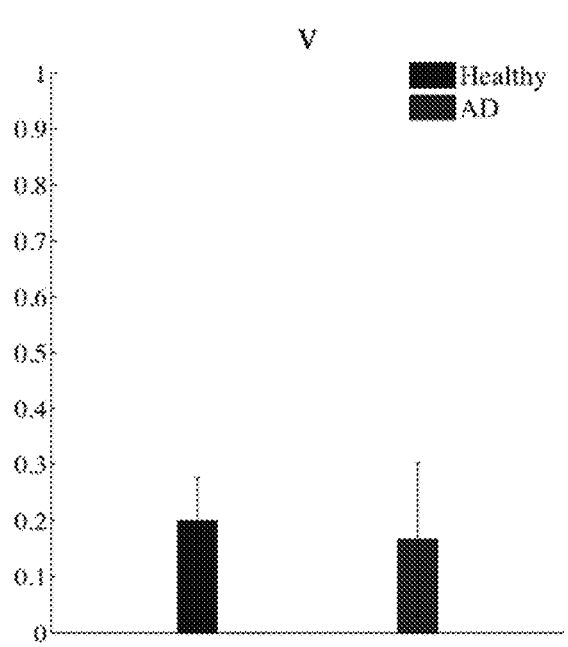
Figure 10F:
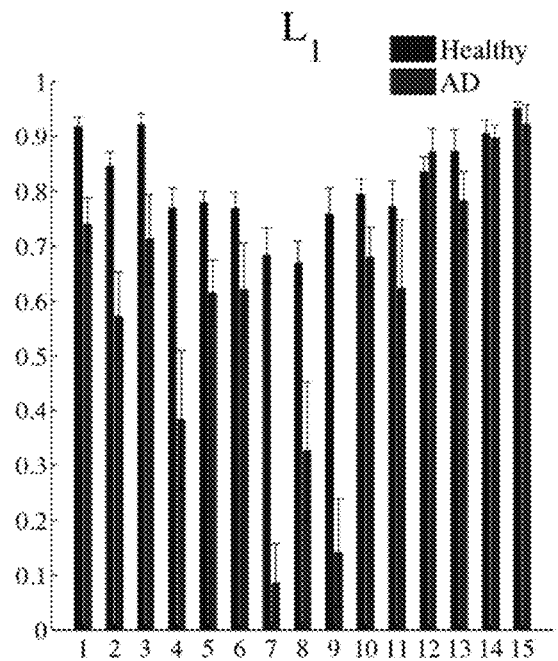
Figure 10G:
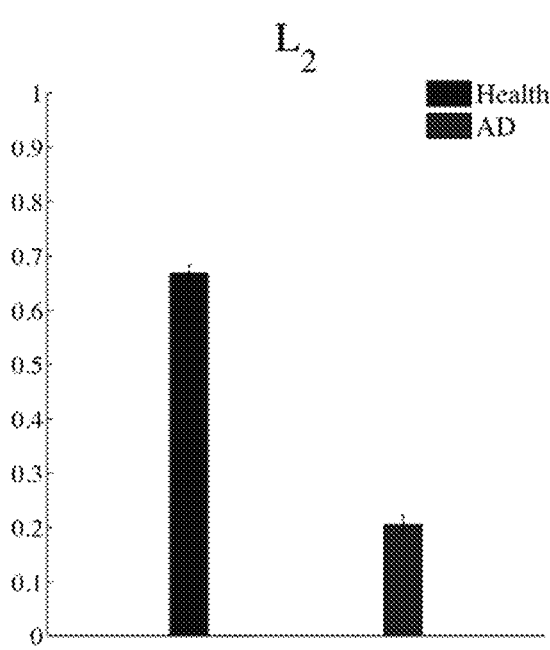
Figure 10H:
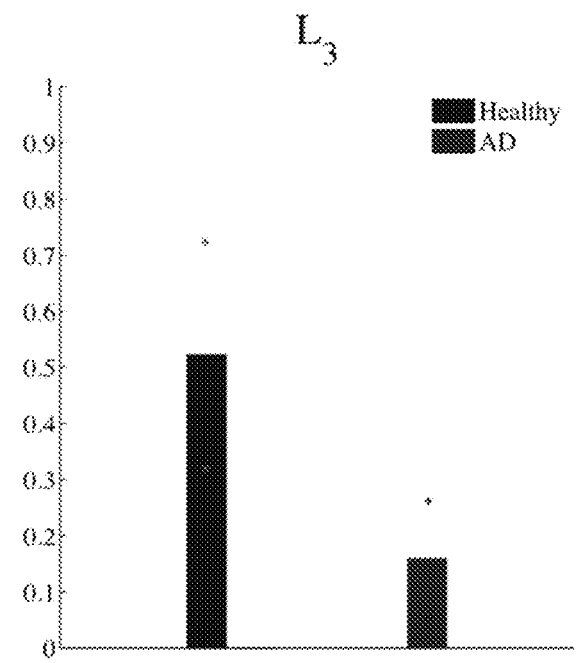

Examining the ADAS-Cog HMM For Stationarity When Applied to AVLT Data: FIGS. 10A-10H show cognitive process parameter probabilities using the AVLT recall task data applied to the HMM developed for the ADAS-Cog recall task. The only modification of the HMM at this point was to include an additional delayed retrieval parameter, $L_3$, and increase the number of list items to 15. FIG. 10A shows the r parameter. FIG. 10B shows the t parameter. FIG. 10C shows the a parameter. FIG. 10D shows the b parameter. FIG. 10E shows the v parameter. FIG. 10F shows the $L_1$ parameter. FIG. 10G shows the $L_2$ parameter. FIG. 10H shows the $L_3$ parameter.

The r and t parameters show large, unexpected values; AD subjects sometimes show better performance than normal aging subjects (e.g., item 14, r parameter; items 7 to 9, t parameter). These parameters are difficult to interpret in any consistent or logical way, and any number of problems can be causing the parameters to look the way they do. For example, it is possible that the model is too simple to capture the signal from a more complex experiment (i.e., AVLT), or it is possible that the data may be too noisy, in which case the structure of the model will remain the same but changes on the parameters might suffice. A solution for the former requires modifications to the structure of the model such that the number of transitions and/or states might change. However, it is first worth determining if the underlying parameter distribution is stationary over trials.

Figure 11A:
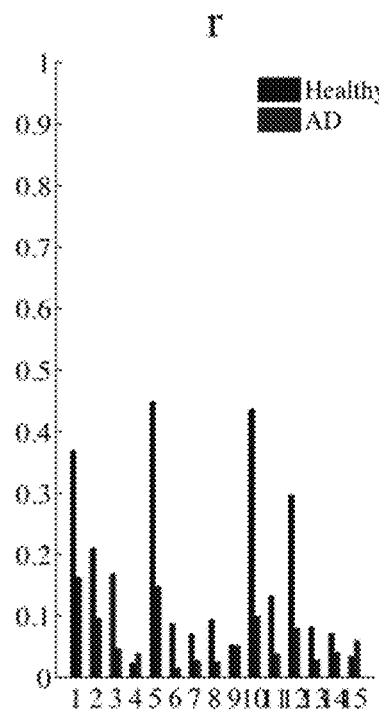
FIGS. 11A-11L show a comparison of cognitive process parameter values generated for different study-test trials.
Figure 11B:
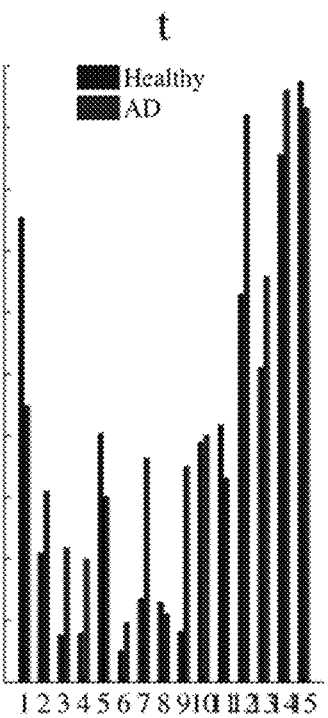
Figure 11C:
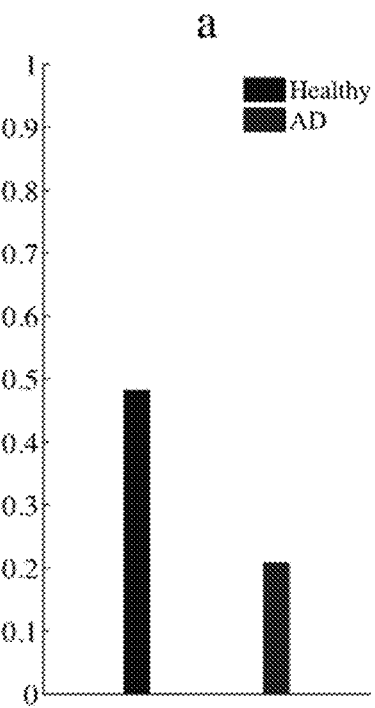
Figure 11D:
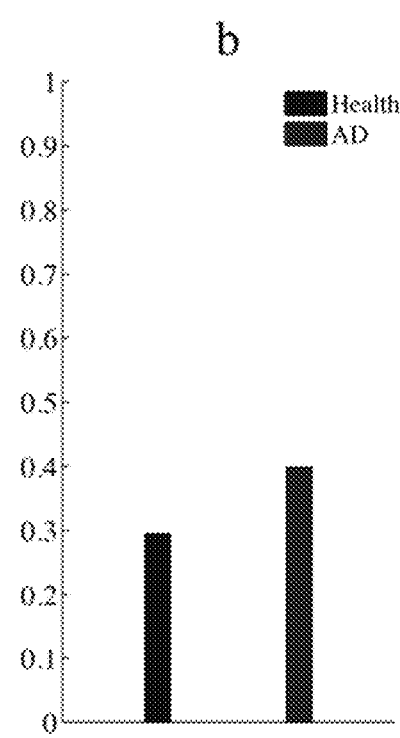
Figure 11E:
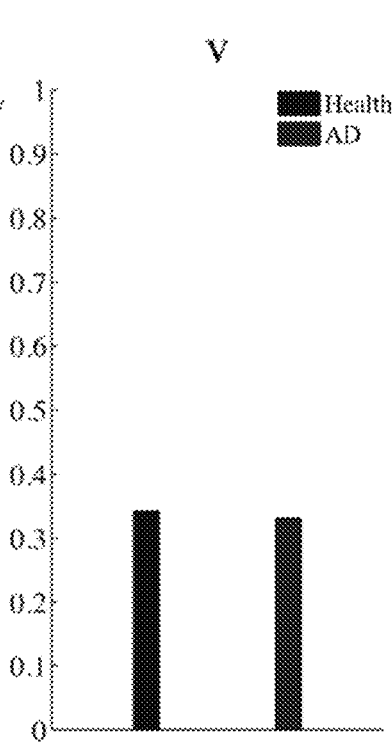
Figure 11F:
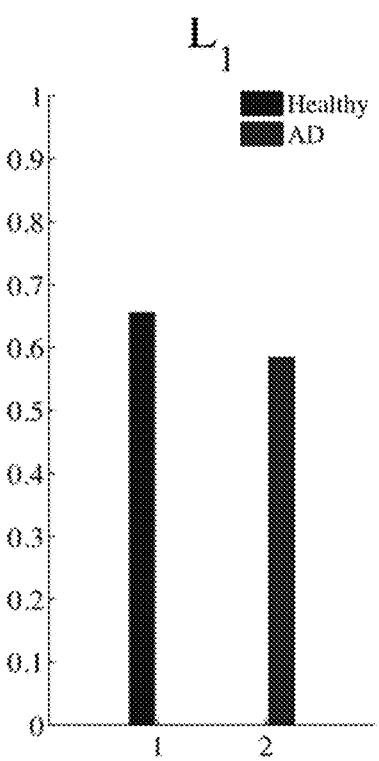

We examined this possible violation of an HMM core assumption by using the same, slightly modified, ADAS- Cog HMM to generate cognitive process parameter values derived for different trial sets. FIGS. 11A-11L show a comparison of cognitive process parameter values generated for different study-test trials. FIG. 11A shows the r parameter derived from the first three study-test trials. FIG. 11B shows the t parameter derived from the first three study-test trials. FIG. 11C shows the a parameter derived from the first three study-test trials. FIG. 11D shows the b parameter derived from the first three study-test trials. FIG. 11E shows the v parameter derived from the first three study-test trials. FIG. 11F shows the $L_1$ parameter derived from the first three study-test trials.

Figure 11G:
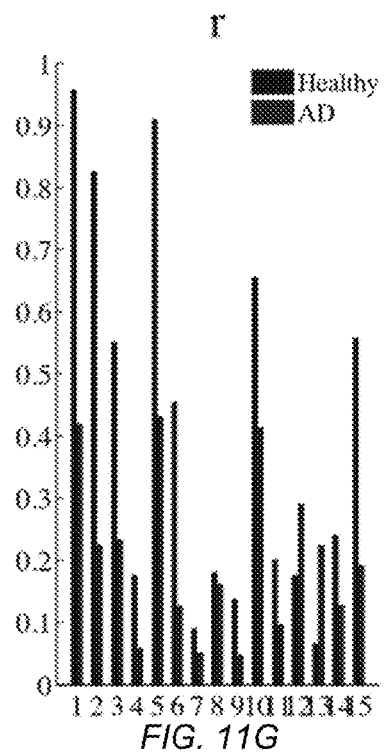
Figure 11H:
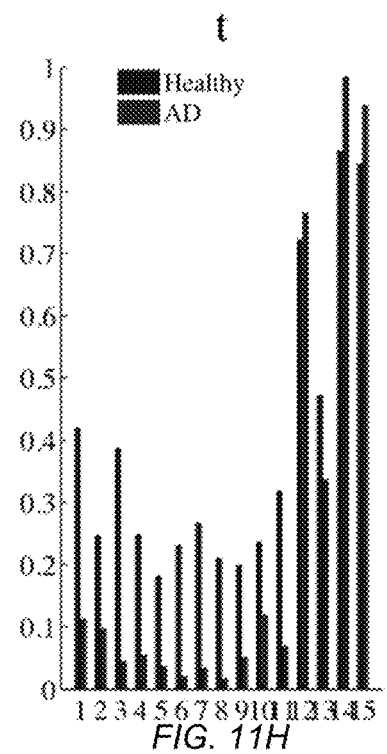
Figure 11I:
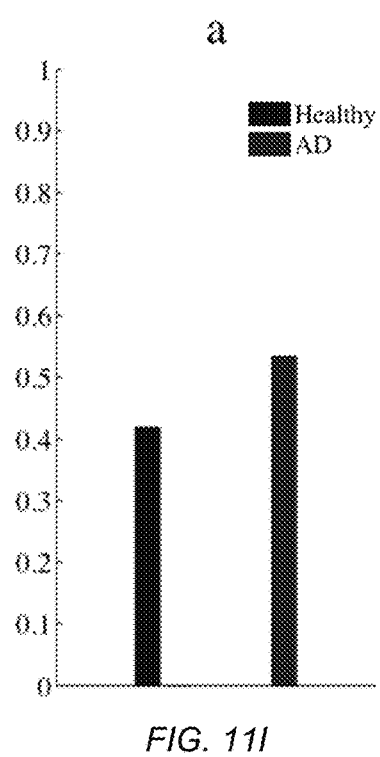
Figure 11J:
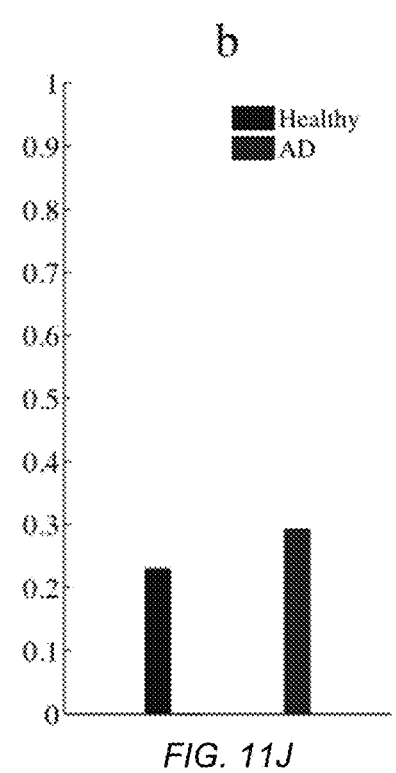
Figure 11K:
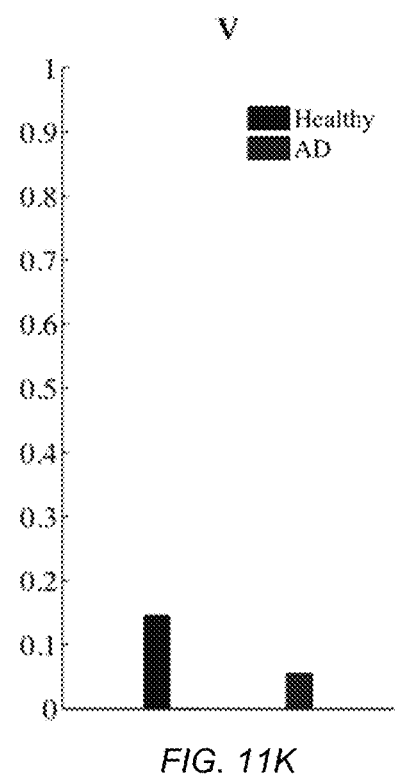
Figure 11L:
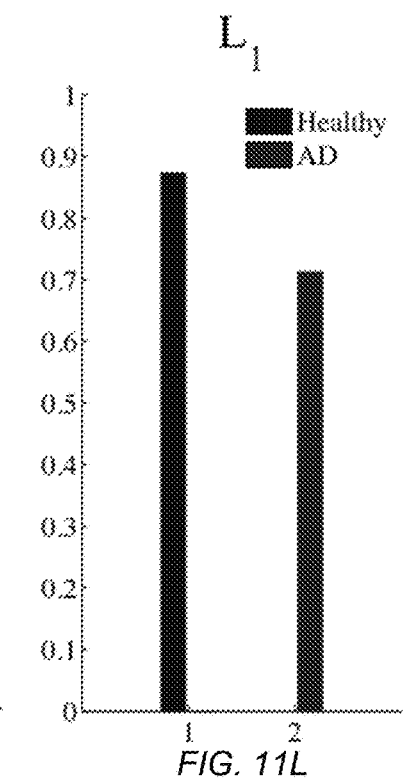

In comparison, FIG. 11G shows the r parameter derived from the last three study-test trials. FIG. 11H shows the t parameter derived from the last three study-test trials. FIG. 11I shows the a parameter derived from the last three study-test trials. FIG. 11J shows the b parameter derived from the last three study-test trials. FIG. 11K shows the v parameter derived from the last three study-test trials. FIG. 11L shows the $L_1$ parameter derived from the last three study-test trials. Comparing the cognitive process parameter values shown in FIGS. 11A-11L, if the parameters do not show the patterns seen before with the ADAS-Cog task data, it could mean that the model is the problem. If the parameter patterns are shown but only on certain trials of the data, then it could mean that the data may be the problem.

For the last three study-test trials, it would be incorrect to assume that the starting vector of the cognitive state sequence is [1 0 0] for states U, I, and L, because the items may no longer be in state, U. We therefore modified the model to use a different starting vector, namely, [1/3 1/3 1/3]. Comparing the data, the r and t parameters for the AVLT recall task data have similar patterns with those of the ADAS-Cog recall task data. Since the AVLT-derived cognitive process parameters did not show similar patterns to those of the ADAS-Cog data, the parameter distributions of r and t, at least, are not stationary. In other words, AVLT recall task data do not have stationary distributions of their cognitive process parameters over the five study-test trials. This violation of a core HMM assumption should thus be addressed to produce a more widely useable model.

Addressing Violation of HMM Assumption of Stationary Parameter Distributions: To handle recall task data that violate this core HMM assumption, the trial-dependent parameters, $\Gamma(r)$ to $\Gamma(L_1)$, can be introduced as one parameter per study or study-test trial per cognitive process. For the ADAS-Cog task data, no trial-dependent parameters were needed because all cognitive process parameters achieved a stable distribution after one study-test trial. However, for the AVLT task data, trial-dependent parameters were needed for some of the cognitive processes.

Figure 12:
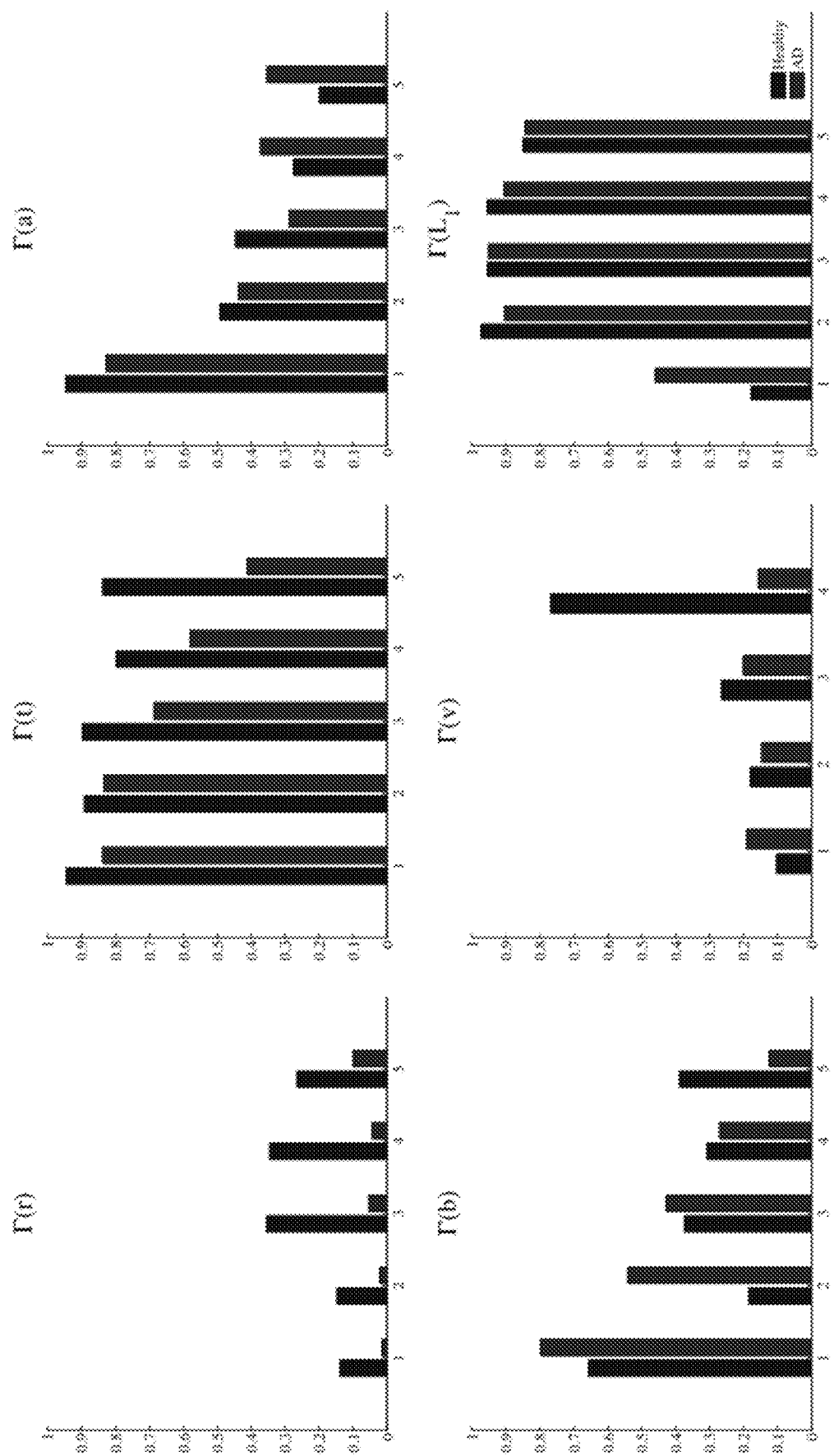
FIG. 12 shows values determined for trial-dependent parameters.

FIG. 12 shows the values of the trial-dependent parameters (labeled as $\Gamma(r)$ to $\Gamma(L_1)$), which range from [0,1] for each study-test trial and for each cognitive process parameter of the AVLT task data. For cognitive processes, r, t, a, b, and L1, their parameter values become stable on study-test trial 3. For cognitive process, v, the value of $\Gamma(v)$ becomes stable on study-test trial 2, and is anomalous study-test trial 4. These cognitive process parameters, therefore require at most, two trial-dependent parameters, for trials 1 and 2. We therefore further modified the HMM by using trial-dependent parameters with each cognitive process to reduce their parameter values for the first two trials.

Figure 13:
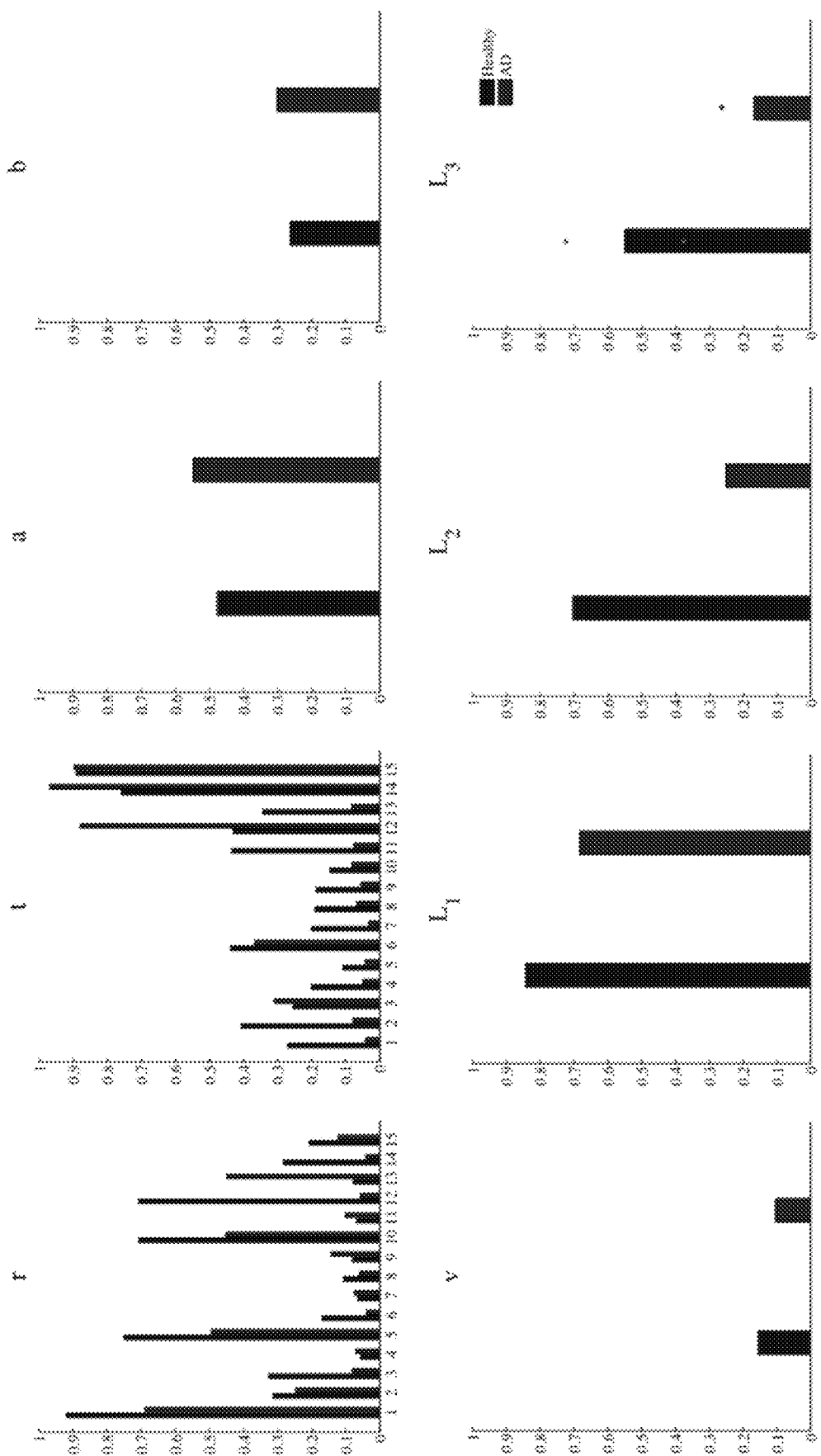
FIG. 13 shows a result of modifying cognitive processes using trial-dependent parameters.

FIG. 13 shows a result of applying the HMM to the AVLT recall task data with trial-dependent parameter reductions only on the first two trials of each parameter. Note that modifying each cognitive process using trial-dependent parameters for the first two trials yields curves with a similar pattern to those obtained with the ADAS-Cog HMM applied to the ADAS-Cog recall task data (compare with FIGS. 10A-11L). FIG. 13 also shows that the idiosyncrasies of certain items, such as the large r parameter values for list items 5, 10 and 12, are not lost. These idiosyncrasies of the AVLT items can be addressed by including order constraints on the parameters r and t. Again, the reduction on the parameters for the two first two trials allows for patterns similar to those found in the ADAS-Cog recall task data to be discovered in the AVLT data.

Figure 14:
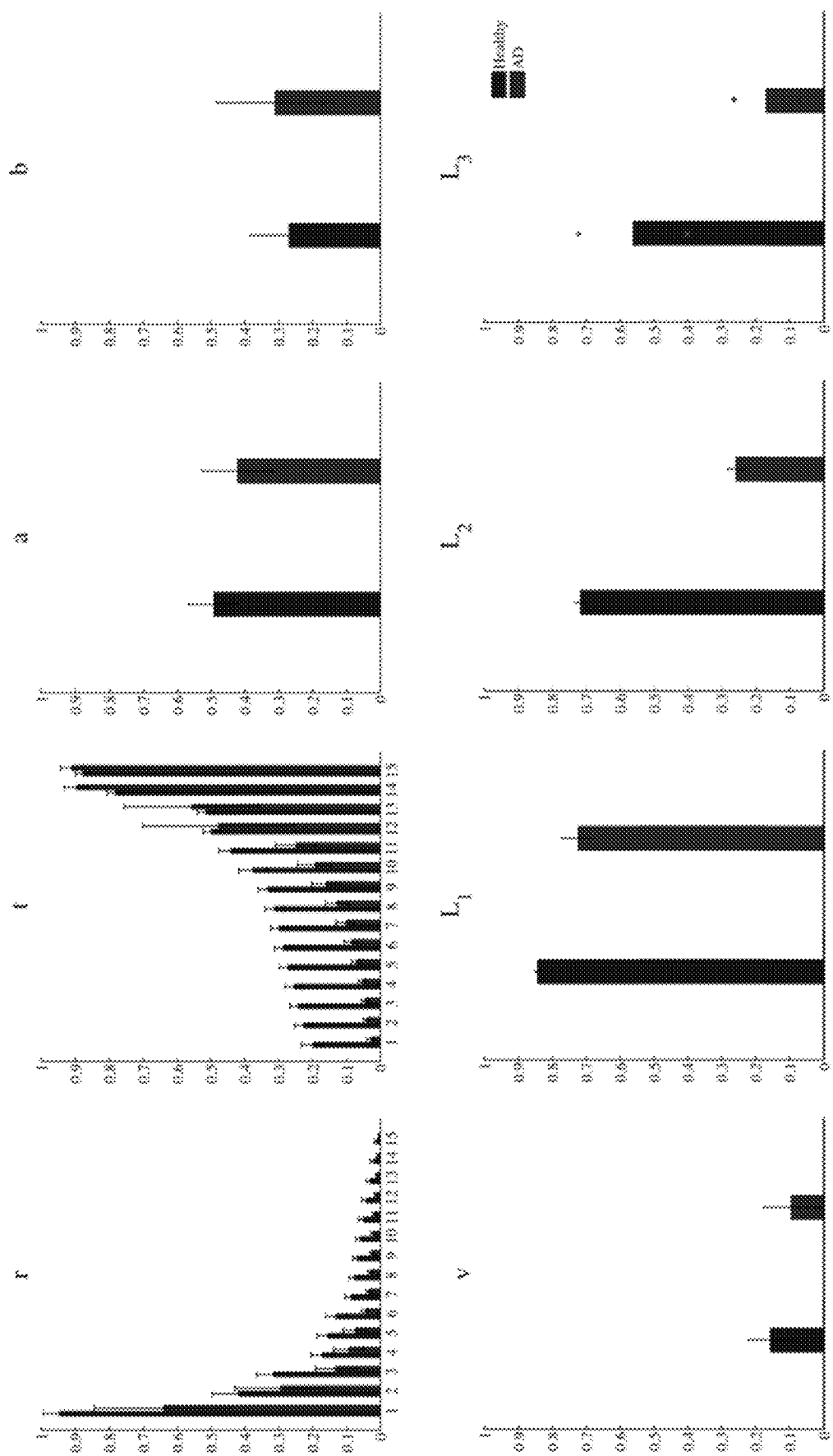
FIG. 14 shows results of the HMM using two trial-dependent parameters with order constraints.

FIG. 14 shows that the order constraints applied to the AVLT HMM instantiation eliminate the idiosyncratic effects of certain AVLT list items. The reduction for the r parameter is rapid for both the Healthy and AD subjects. This might be due to the complicated nature of a longer list tests, or it could be that the two groups might involve participants with a wider range of impairments. The additional parameter, $L_3$, for the one hour delayed test trial shows almost no reduction compared to $L_2$, the retrieval strength at the 5-minute delayed test trial.

The two asterisks above the $L_3$ parameters indicate that words correctly recalled on the 5-minute, delayed test trial had a very similar probability of being recalled on the one hour delayed test trial for both normal and AD groups. This finding suggests that when AD subjects recall words after a 5-minute delay, they retain their ability to recall them even after a much longer delay. This finding is consistent with a considerable literature suggesting that recall tests have a big effect on subsequent recall performance and also on learning. This finding is further supported by the results of parameter, b, which is the same for AD and normal subjects. The cognitive process of the b parameter is to encode and store items in state, L, when they are recalled during study-test trials. The normality of the b parameter in AD means that cognitive therapy and drug development could enhance episodic (hippocampal) memory by increasing the probability of retrieval during study-test trials, or in the real world, while learning new information.

The modifications of the ADAS-Cog HMM instantiation embodied within the AVLT HMM instantiation have resulted in the model's ability to reliably measure cognitive processes from three different subject populations assessed with two very different recall tasks. Consequently, the AVLT HMM can account for: 1) the effects of any ordering of study list items across study trials; 2) any number of study and/or test trials; and 3) varying learning periods, study trials, or exposure times needed for each model parameter to achieve a stationary distribution.

This extended model can also use a different method of measuring the effects on storage and retrieval due to item ordering across study trials. Rather than determining the effects of list position by computing the distances of each item's position in each trial from the trial's first and last positions and using these distances to estimate the degree of primacy and recency of each item in each trial, the distance of each item's position from the first and last position in each trial need not be used to estimate the model's parameters. In addition, the model can be designed to separately measure item storage and retrieval to and from distinct cognitive states, rather than measuring storage and retrieval together for different cognitive states.

A further adaptation can be made in some implementations in the context of measuring cognition in individuals and groups in clinical research and clinical patient care settings. The HMM can be modified to become a Finite Mixture Markov (FMM) model. Finite Mixture Markov models classify individuals into one of two groups when the groups are unknown a priori. The FMM model assumes that there are two latent groups, whose distinct parameter values are derived from the observed data applied to the HMM. In the present FMM model, the observed data are the item response patterns of the ADAS-Cog wordlist memory recall task. Each subject is classified into the group whose parameter values are closest to those of the subject.

Figure 15:
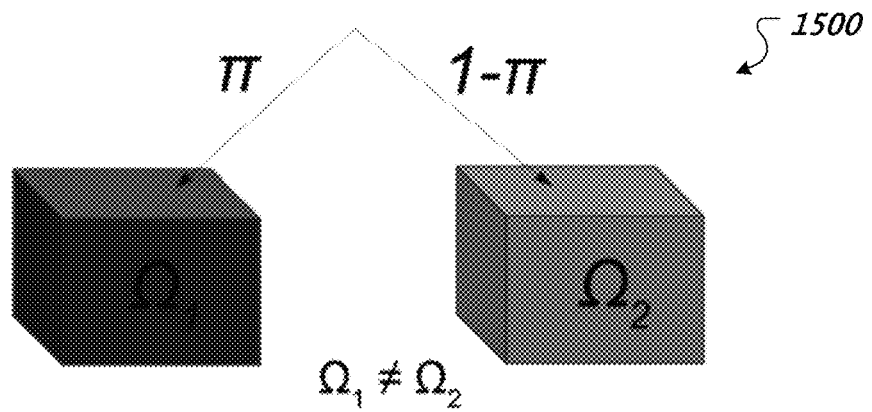
FIG. 15 shows a visual representation of a Finite Mixture Markov Model.

FIG. 15 shows a visual representation of a Finite Mixture Markov Model 1500. The FMM model 1500 has twice as many parameters as the HMM because the second group has its own set (e.g., 52 additional parameters for the ADAS-Cog recall task instantiation). The FMM model has one additional parameter, $\pi$, which represents probability of a subject's membership to one of the groups. The confidence in classifying a subject with the FMM model is defined by the posterior probability of belonging to the specified group.

The two groups, $\Omega_1$ and $\Omega_2$, are defined by distinct sets of parameter values, which are derived from the observed data of the item response patterns. A given subject's probability of classification into each group is determined–$\pi$ for group $\Omega_1$ and 1–$\pi$ for group $\Omega_2$–based on the proximity of their parameter values to those of the groups.

Figure 16:
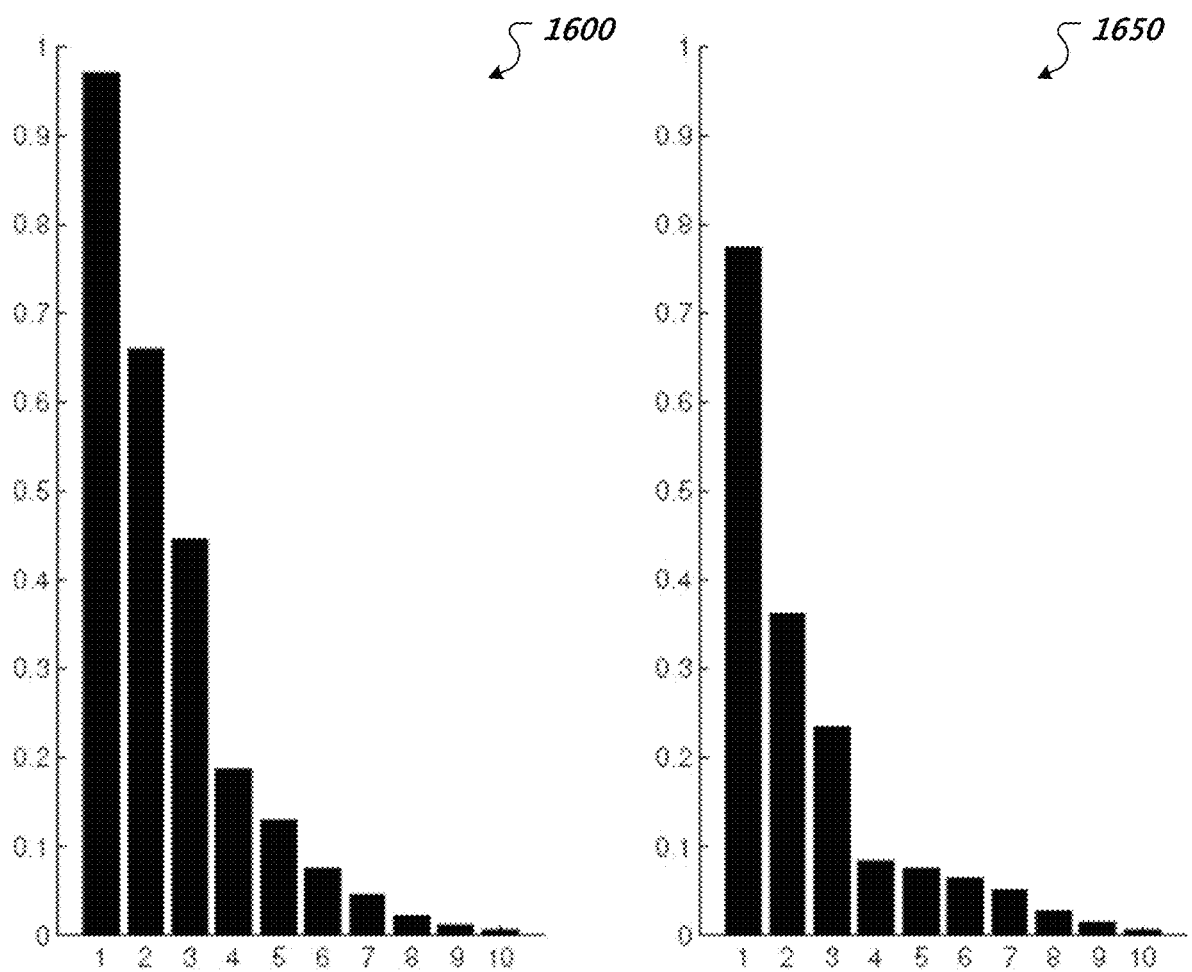
FIG. 16 shows a comparison of cognitively normal and MCI groups using an ADAS-Cog HMM instantiation.

Comparison of Healthy and MCI Groups Using ADAS-Cog Task Data: FIG. 16 shows a comparison of cognitively normal and MCI groups using an ADAS-Cog HMM instantiation. A chart 1600 shows r parameter estimates (probability against word positions) of the transition from the Unlearned into the Learned (short-term memory) states for the cognitively normal subjects of the ADCS. A chart 1650 shows r parameter estimates (probability against word positions) of the transition from the Unlearned into the Learned (short-term memory) states for the MCI subjects of the ADCS. Both groups show a similar pattern of decline in r parameter values with increasing word position, but the values of the MCI group are smaller than the cognitively normal group. Thus, for this ADAS-Cog HMM instantiation, cognitively normal and MCI groups are shown to have a similar pattern of decline in the transition of items from the Unlearned state into the short-term memory state as word list position increases from beginning to end (storage parameter, r). The difference between these two groups is that the absolute values of the r parameters are lower for the MCI group than the cognitively normal group at each word list position.

Figures 17, 18:
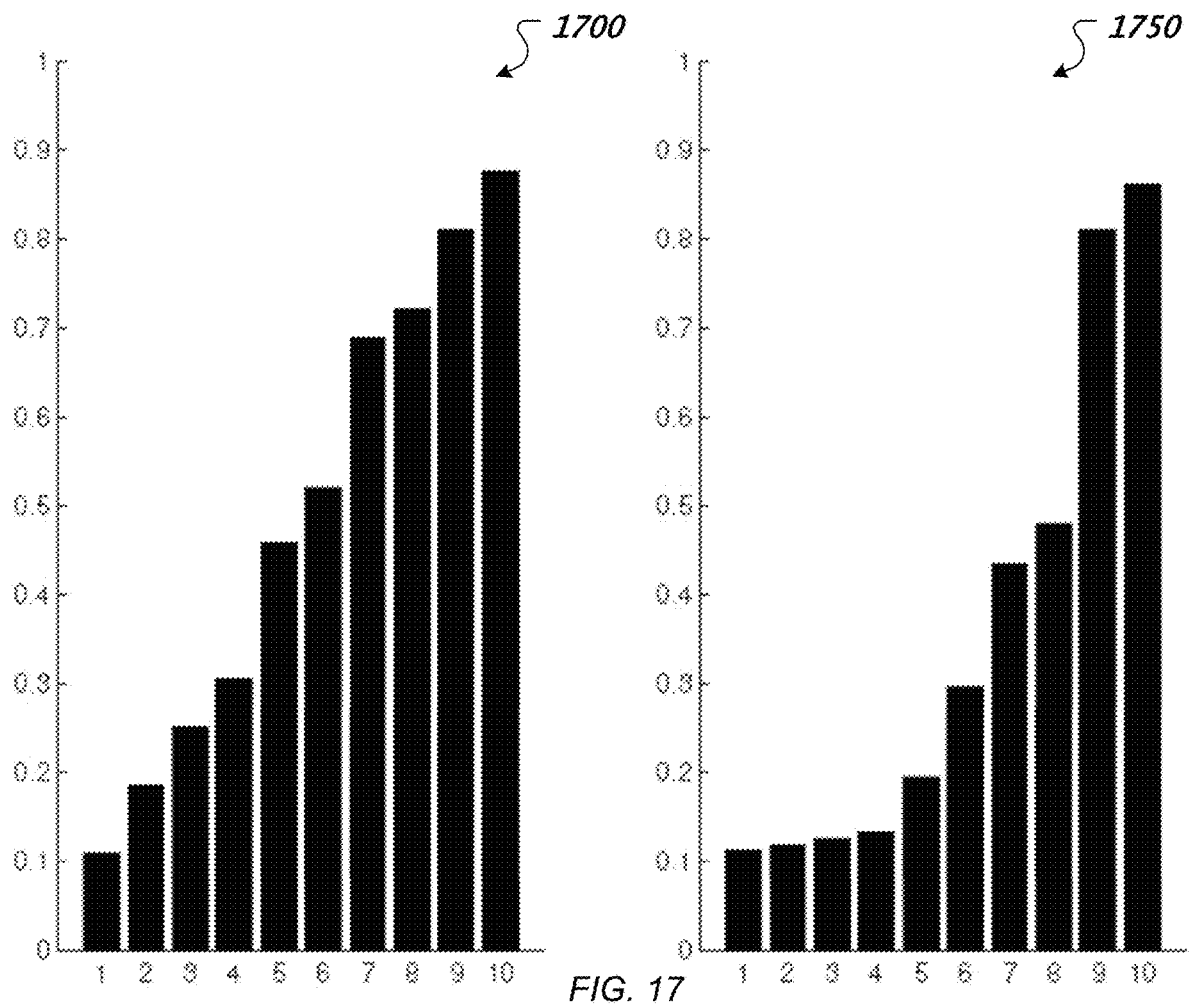
FIG. 17 shows another comparison of cognitively normal and MCI groups using an ADAS-Cog HMM instantiation.
FIG. 18 shows short-term memory retrieval parameter estimates at end of study period and after several minutes delay in cognitively normal and MCI groups of two ADCS studies.

FIG. 17 shows another comparison of cognitively normal and MCI groups using an ADAS-Cog HMM instantiation. A chart 1700 shows t parameter estimates (probability against word positions) of the transition from the Unlearned into the Learned (working memory) states for the cognitively normal subjects of the ADCS. A chart 1750 shows r parameter estimates (probability against word positions) of the transition from the Unlearned into the Learned (working memory) states for the MCI subjects of the ADCS. Both groups show a pattern of increase in t parameter values with increasing word position, but the values of the MCI group show a more flattened rate of increase from word positions 1 to 8 than do the cognitively normal group. Thus, this data derived from the ADAS-Cog model shows that the MCI group retrieves words from working memory less effectively than the cognitively normal group. The shallower rate of increase in retrieval probability for MCI compared to the cognitively normal group means that MCI subjects have reduced retrieval capacity from working memory compared to the cognitively normal group.

FIG. 18 shows short-term memory retrieval parameter estimates at end of study period ($L_1$) and after several minutes delay ($L_2$) in cognitively normal and MCI groups of two ADCS studies. Charts 1800 and 1850 show that retrieval from short-term memory during study-test trials ($L_1$) is only slightly lower in MCI compared to normal subjects, which means that not all cognitive processes are affected by MCI. However, charts 1825 and 1875 show that delayed retrieval from short-term memory ($L_2$), is much more impaired for MCI compared to normal subjects. This means that in amnestic MCI, retrieval from short-term memory decays more rapidly than in normal aging.

Figure 19:
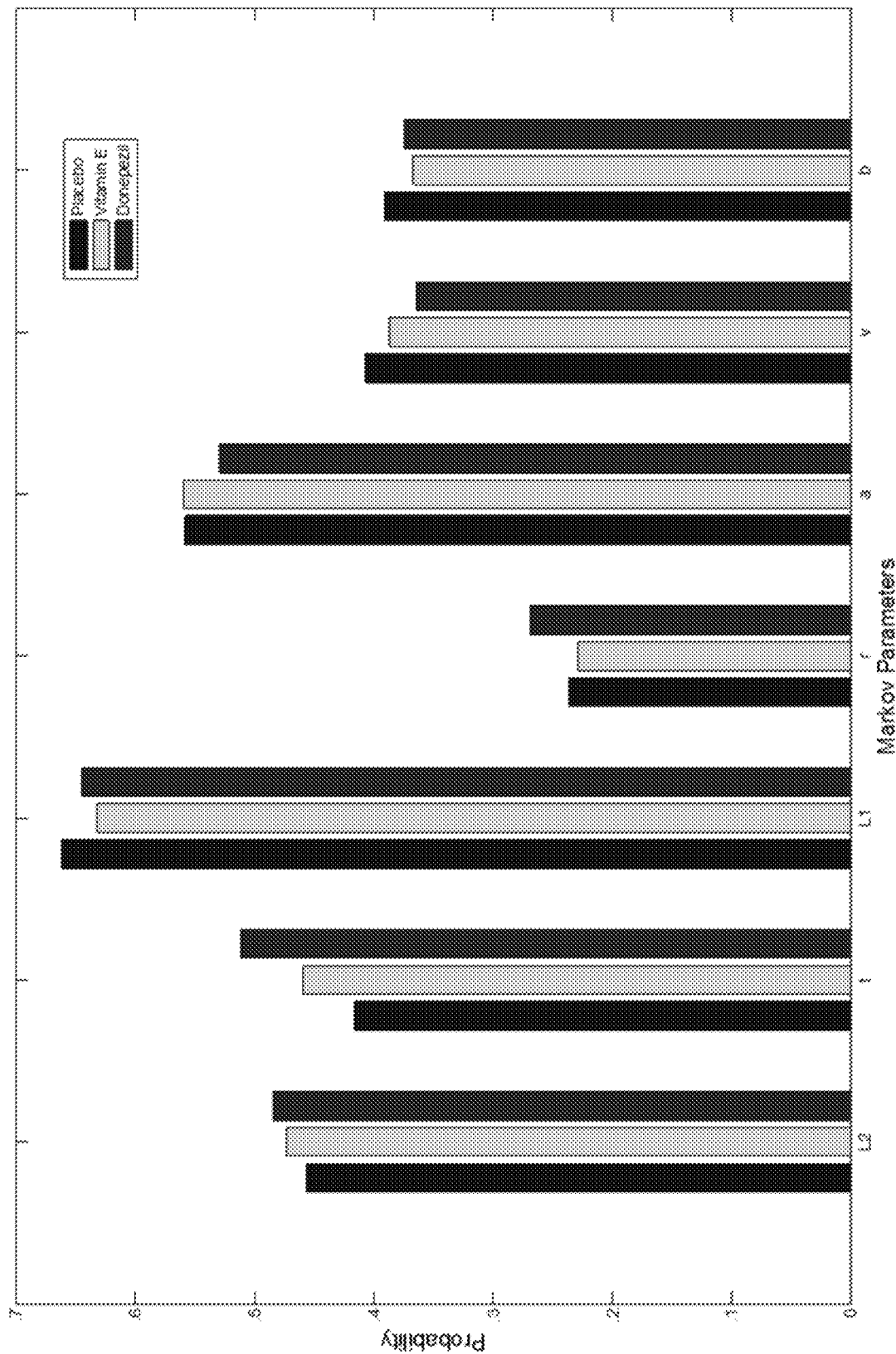
FIG. 19 shows ADAS-Cog HMM instantiation estimated parameter values per cognitive process derived from ADAS-Cog recall task data per treatment group of the ADCS study of amnestic MCI.

Comparison of Normal vs. AD using AVLT Task Data: FIG. 19 shows ADAS-Cog HMM instantiation estimated parameter values per cognitive process (r, a, t, v, b, L1, L2) derived from ADAS-Cog recall task data per treatment group (Placebo, Vitamin E, Donepezil) of the ADCS study of amnestic MCI. The ADAS-Cog wordlist memory task item response data from the ADCS amnestic MCI clinical trial comparing placebo, vitamin E and donepezil were analyzed using the HMMs described above. Five of the memory storage and retrieval parameters (r, a, v, b, t) were estimated for each of the 10 word list positions, and 1 parameter was estimated for each of $L_1$ and $L_2$.

In FIG. 19, each bar shows one of the seven working memory (WM) or short-term memory (STM) storage (r, a, v, b) or retrieval (t, L1, L2) parameters for the three treatment groups of the ADCS study (blue=placebo, green=Vitamin E, red=Donepezil). Each bar's storage or retrieval parameter is collapsed over word list positions in the study trials, over the 36 months of assessments, and over subjects. Each bar therefore provides an overall perspective of the differences in the cognitive processes represented by the WM and STM storage and retrieval parameters across treatment groups.

The cognitive process parameter, t (retrieval from state, I), significantly differs across treatment group (P<0.0001) over the 36 month study. These treatment group differences were in the same direction as those reported in the original ADCS analysis. For the donepezil vs. placebo comparison, mildly significant differences (P<0.05 or P<0.01) were found in the original ADCS study for the modified ADAS-Cog, the ADAS-Cog recall and other memory tasks only during the first 18 months. The clinical meaningfulness of an improvement in the WM retrieval parameter, t, is that subjects can more effectively retrieve information from working memory when performing ongoing activities of daily living and communicating to others. Such an improvement in WM retrieval with Vitamin E therapy (which also occurred with donepezil) may explain recently reported findings of a 20% reduction in rate of decline of functional activities of daily living in patients receiving Vitamin E, 2000 IU daily.

The ADAS-Cog HMM analysis of the ADCS study identified significant treatment effects of vitamin E and donepezil that were only of borderline significance in previous analyses. Furthermore, the model identifies how these treatments affect the underlying cognitive processes involved in memory task performance.

Classification using Finite Mixture Model: Two results were obtained using the FMM model, both of which are on different data sets. The first result is taken from the behavioral data of 612 MCI ADCS subjects of the Placebo, Vitamin E, and Donepezil trial, plus a separate ADCS study of 112 cognitively normal subjects. We omitted this prior cognitive severity knowledge from the FMM Model in our analysis and assigned an uninformative prior on it to see how well it would classify each participant. The model correctly identified 105/112 (93%) of the cognitively normal subjects. However, MCI subjects were not all classified as being impaired. There may be separate levels of impairment among MCI subjects, so that a two-group design may be inappropriate. This result shows that, using the ADAS-Cog HMM applied to ADAS-Cog recall task data can correctly identify the cognitively normal subjects, but that a separate model may be useful to categorize MCI subjects into distinct subgroups.

A second analysis used the ADAS-Cog HMM to analyze ADAS-Cog recall task from 14 AD participants in the Myriad phase III FDA trial of flurizan vs. placebo. Experienced clinicians categorized all participants, using the Functional Assessment Staging Test (FAST) procedure, into normal cognition (FAST 1), early MCI (FAST 2), late MCI (FAST 3) and mild dementia (FAST 4). The FMM Model was able to effectively separate the FAST stage 1 and 2 subjects from FAST stage 3 and 4 subjects. These preliminary results of the FMM model show its utility in latent classification when using the ADAS-Cog HMM applied to recall task data.

In summary, combining a quantitative model with established psychological theory, as described herein, can disambiguate the latent cognitive processes from the behavioral measures (item responses) collected from a multiple item free recall task. The machinery of the class of HMMs was adapted to accomplish this purpose and clarified the latent cognitive processes underlying an item recall task. The ADAS-Cog and AVLT HMM instantiations showed close agreement in the patterns of the cognitive process parameters, plus showed that primacy and recency effects are a byproduct of underlying latent cognitive processes that can be disentangled from behavioral measures. The substantive differences between AVLT and ADAS-Cog recall tasks are appropriately handled by the more general HMM instantiation derived from analysis of the AVLT recall task data. This development of a more general HMM instantiation resulted in a new approach to satisfy the core HMM assumption of stationary parameter distributions over time and trials.

The generality of HMM systems and techniques described herein is such that it can measure underlying cognitive processes of recall tasks using any number of list items, any number of study, study-test and test trials, and can resolve the problem of non-stationary cognitive process parameter distributions across time and trials. We have also shown that these HMM systems and techniques can be used to assess and monitor individuals, such as is often required in medical practice.

The HMM systems and techniques described herein adapt previous research to facilitate distinguishing normal from cognitively impaired subjects as well as measuring disease progression and treatment effects. The Finite Mixture Markov model has the capability of discriminating groups of fundamental importance in the field of Alzheimer's disease, such as those who differ by a given biomarker. As will be appreciated, various computer systems can be used to implement the systems and techniques described herein and perform computational analysis item response data to assess states of cognition.

Figure 20:
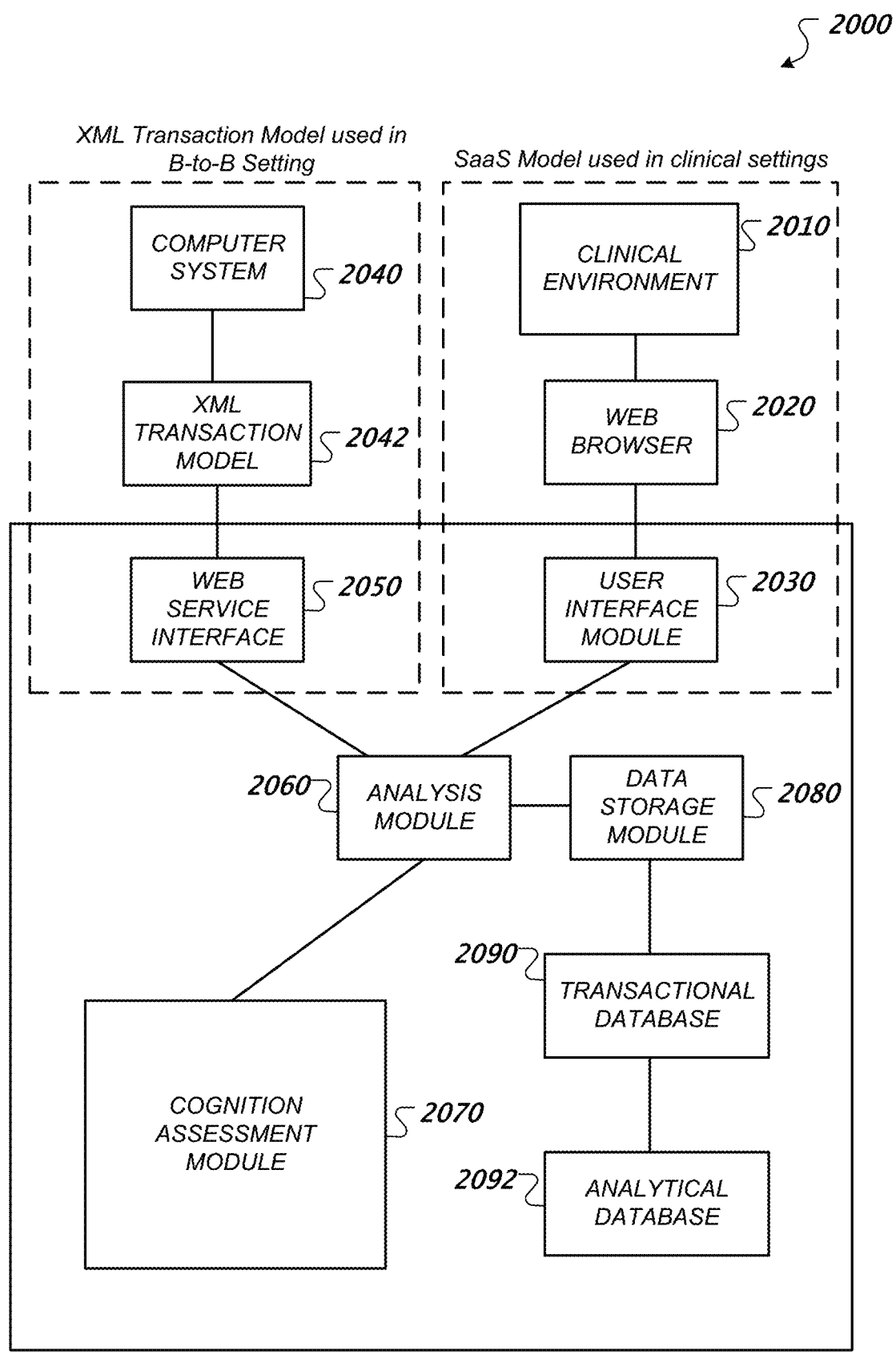
FIG. 20 shows another example of a system used to generate an analysis of data for a test of cognition.

FIG. 20 shows another example system 2000 used to generate an analysis of data for a test of cognition. The example system described can perform a variety of functions including data analysis, storage and viewing, and remote access and storage capabilities useful for generating and using the analysis techniques described herein.

A Software as a Service (SaaS) model can provide network based access to the software used to generate the analysis. This central management of the software can provide advantages, which are well known in the art, such as offloading maintenance and disaster recovery to the provider. A user, for example, a test administrator within a clinical environment 2010, can access test administration software within the test administration system via a web browser 2020. A user interface module 2030 receives and responds to the test administrator interaction.

In addition, a customer's computer system 2040 can access software and interact with the test administration system using an eXtensible Markup Language (XML) transactional model 2042. The XML framework provides a method for two parties to send and receive information using a standards-based, but extensible, data communication model. A web service interface 2050 receives and responds to the customer computer system 2040 in XML format. For example, an XML transactional model can be useful for storage and retrieval of the structured data relating to the stochastic model(s) of cognitive processes (e.g., Hidden Markov Models and Finite Mixture Markov Models) and the item response data.

An analysis module 2060 analyses inputs from the web service interface 2050 and the user interface module 2030, and produces test results to send. The analysis module uses a cognition assessment module 2070 to perform the test analysis using the stochastic model(s), as described herein. The cognition assessment module 2070 can, for example, incorporate Hidden Markov Model and Finite Mixture Markov Model as described above in this specification.

A data storage module 2080 transforms the test data collected by the user interface module 2030, web service interface 2050, and the resulting data generated by the analysis module 2060 for permanent storage. A transactional database 2090 stores data transformed and generated by the data storage module 2080. For example, the transactional database can keep track of individual writes to a database, leaving a record of transactions and providing the ability to roll back the database to a previous version in the event of an error condition. An analytical database 2092 can store data transformed and generated by the data storage module 2080 for data mining and analytical purposes.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a cross-platform runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims.

What is claimed is:

1. A computer-implemented method comprising:
   receiving data comprising responses, and lack thereof, for items of a cognitive test, wherein the cognitive test comprises test trials;
   processing the data using a Finite Mixture Markov (FMM) model of a cognitive process, wherein the FMM model of the cognitive process
   (i) represents recall, identification or recognition of an item in at least one of the test trials using distinct cognitive states, and
   (ii) adjusts separate memory storage and retrieval parameters for each of the distinct cognitive states to account for position of the items in each respective trial of the test trials; and
   classifying individuals into one of two groups that differ by a given biomarker using results of the processing the data using the FMM model of the cognitive process.

2. The computer-implemented method of claim 1, wherein the distinct cognitive states comprise three cognitive states being an unlearned state, an intermediate state, and a learned state.

3. The computer-implemented method of claim 2, wherein each of the memory storage and retrieval parameters have an assigned subscript corresponding to an item's position in a trial.

4. The computer-implemented method of claim 3, wherein the test trials are at least three trials, at least two items of the at least three trials are free to be placed in different list positions in separate administrations of individual trials of the at least three trials, and respective ones of the subscripts correspond to an item's position in respective ones of the at least three trials.

5. The computer-implemented method of claim 2, wherein processing the data using the FMM model comprises computing a probability of a given item's response pattern using a set of all possible cognitive state sequences except for cognitive state sequences that transition from the learned state to the intermediate state, from the learned state to the unlearned state, or from the intermediate state to the unlearned state.

6. The computer-implemented method of claim 2, wherein the given biomarker is cerebrospinal fluid.

7. The computer-implemented method of claim 2, wherein the given biomarker is amyloid.

8. The computer-implemented method of claim 2, wherein classifying the individuals comprises measuring disease progression.

9. The computer-implemented method of claim 2, wherein classifying the individuals comprises measuring treatment effects.

10. A system comprising:
a user device; and
one or more computers operable to interact with the user device, and the one or more computers being configured to (i) receive data comprising responses, and lack thereof, for items of a cognitive test, wherein the cognitive test comprises test trials, (ii) process the data using a Finite Mixture Markov (FMM) model of a cognitive process, wherein the FMM model of the cognitive process (a) represents recall, identification or recognition of an item in at least one of the test trials using distinct cognitive states, and (b) adjusts separate memory storage and retrieval parameters for each of the distinct cognitive states to account for position of the items in each respective trial of the test trials, and (iii) classify individuals into one of two groups that differ by a given biomarker using results of the processing the data using the FMM model of the cognitive process.

11. The system of claim 10, wherein the distinct cognitive states comprise three cognitive states being an unlearned state, an intermediate state, and a learned state.

12. The system of claim 11, wherein each of the memory storage and retrieval parameters have an assigned subscript corresponding to an item's position in a trial.

13. The system of claim 12, wherein the test trials are at least three trials, at least two items of the at least three trials are free to be placed in different list positions in separate administrations of individual trials of the at least three trials, and respective ones of the subscripts correspond to an item's position in respective ones of the at least three trials.

14. The system of claim 11, wherein the one or more computers are configured to compute a probability of a given item's response pattern using a set of all possible cognitive state sequences except for cognitive state sequences that transition from the learned state to the intermediate state, from the learned state to the unlearned state, or from the intermediate state to the unlearned state.

15. The system of claim 11, wherein the given biomarker is cerebrospinal fluid.

16. The system of claim 11, wherein the given biomarker is amyloid.

17. The system of claim 11, wherein the one or more computers are configured to measure disease progression.

18. The system of claim 11, wherein the one or more computers are configured to measure treatment effects.

19. A non-transitory computer-readable medium encoding a computer program product operable to cause data processing apparatus to perform operations comprising:

receiving data comprising responses, and lack thereof, for items of a cognitive test, wherein the cognitive test comprises test trials;
processing the data using a Finite Mixture Markov (FMM) model of a cognitive process, wherein the FMM model of the cognitive process
  (i) represents recall, identification or recognition of an item in at least one of the test trials using distinct cognitive states, and
  (ii) adjusts separate memory storage and retrieval parameters for each of the distinct cognitive states to account for position of the items in each respective trial of the test trials; and
classifying individuals into one of two groups that differ by a given biomarker using results of the processing the data using the FMM model of the cognitive process.

20. The non-transitory computer-readable medium of claim 19, wherein the distinct cognitive states comprise three cognitive states being an unlearned state, an intermediate state, and a learned state.

21. The non-transitory computer-readable medium of claim 20, wherein each of the memory storage and retrieval parameters have an assigned subscript corresponding to an item's position in a trial.

22. The non-transitory computer-readable medium of claim 21, wherein the test trials are at least three trials, at least two items of the at least three trials are free to be placed in different list positions in separate administrations of individual trials of the at least three trials, and respective ones of the subscripts correspond to an item's position in respective ones of the at least three trials.

23. The non-transitory computer-readable medium of claim 20, wherein processing the data using the FMM model comprises computing a probability of a given item's response pattern using a set of all possible cognitive state sequences except for cognitive state sequences that transition from the learned state to the intermediate state, from the learned state to the unlearned state, or from the intermediate state to the unlearned state.

24. The non-transitory computer-readable medium of claim 20, wherein the given biomarker is cerebrospinal fluid.

25. The non-transitory computer-readable medium of claim 20, wherein the given biomarker is amyloid.

26. The non-transitory computer-readable medium of claim 20, wherein classifying the individuals comprises measuring disease progression.

27. The non-transitory computer-readable medium of claim 20, wherein classifying the individuals comprises measuring treatment effects.

* * * * *